(12) United States Patent
Berman et al.

(10) Patent No.: US 10,786,648 B2
(45) Date of Patent: Sep. 29, 2020

(54) APPARATUS, METHOD, AND SYSTEM FOR PROVIDING TUNABLE CIRCADIAN LIGHTING AT CONSTANT PERCEIVED BRIGHTNESS AND COLOR

(71) Applicant: Musco Corporation, Oskaloosa, IA (US)

(72) Inventors: Samuel M. Berman, San Francisco, CA (US); Bradley D. Schlesselman, Oskaloosa, IA (US); Jason T. Schutz, Oskaloosa, IA (US)

(73) Assignee: Musco Corporation, Oskaloosa, IA (US)

( * ) Notice: Subject to any disclaimer, the term of this patent is extended or adjusted under 35 U.S.C. 154(b) by 347 days.

(21) Appl. No.: 15/611,511

(22) Filed: Jun. 1, 2017

(65) Prior Publication Data

US 2017/0348506 A1   Dec. 7, 2017

Related U.S. Application Data

(60) Provisional application No. 62/345,559, filed on Jun. 3, 2016.

(51) Int. Cl.
*A61M 21/00* (2006.01)
*H05B 45/10* (2020.01)
(Continued)

(52) U.S. Cl.
CPC ............. *A61M 21/00* (2013.01); *H05B 45/10* (2020.01); *H05B 45/20* (2020.01); *H05B 47/16* (2020.01);
(Continued)

(58) Field of Classification Search
CPC ...... A61M 21/00–02; A61N 2005/0651–0653; Y02B 20/30–72; H05B 45/00–28
See application file for complete search history.

(56) References Cited

U.S. PATENT DOCUMENTS

| | | |
|---|---|---|
| 5,015,924 A | 5/1991 | Berman et al. |
| 6,631,987 B2 | 10/2003 | Reichow et al. |

(Continued)

FOREIGN PATENT DOCUMENTS

| | | |
|---|---|---|
| CN | 101678209 A | 3/2010 |
| CN | 102573227 A | 7/2012 |

(Continued)

OTHER PUBLICATIONS

Musco Corporation, PCT/US2017/035501 filed Jun. 1, 2017, "International Search Report and Written Opinion of the International Searching Authority", dated Sep. 15, 2017.
(Continued)

*Primary Examiner* — Thaddeus B Cox
(74) *Attorney, Agent, or Firm* — McKee, Voorhees & Sease, PLC

(57) ABSTRACT

The newly discovered retinal ganglion cell photoreceptor melanopsin absent in the central fovea of the eye but distributed throughout the remaining human retinal body provides both non-visual biological/physiological input inducing circadian entrainment, and visual input affecting perceived brightness; this perceived brightness is not the object brightness commonly associated with luminance and perceived color of an object in central view, but the perception of brightness of a whole space or task background. Discussed are improvements to circadian lighting systems based on melanopsin stimulation whereby ambient and/or device background lighting may be temporally tuned over a range of prescribed color temperatures from a first subset of lighting having a higher melanopic content to a second subset of lighting having a lower melanopic content or vice versa in accordance with a desired circadian cycle, and in a manner where net light output is of a constant perceived brightness and color throughout temporal tuning.

10 Claims, 29 Drawing Sheets

(51) Int. Cl.
    *H05B 45/20*     (2020.01)
    *H05B 47/16*     (2020.01)
    *H05B 47/19*     (2020.01)
    *A61N 5/06*     (2006.01)

(52) U.S. Cl.
    CPC ..... *H05B 47/19* (2020.01); *A61M 2021/0044* (2013.01); *A61M 2021/0055* (2013.01); *A61M 2021/0083* (2013.01); *A61N 5/0618* (2013.01); *A61N 2005/0626* (2013.01); *A61N 2005/0651* (2013.01); *Y02B 20/42* (2013.01)

(56) References Cited

U.S. PATENT DOCUMENTS

| | | | |
|---|---|---|---|
| 6,681,110 | B1 | 1/2004 | Crookham et al. |
| 8,028,706 | B2 | 10/2011 | Skene et al. |
| 8,258,722 | B2 | 9/2012 | Swoboda et al. |
| 8,378,574 | B2 | 2/2013 | Schlangen et al. |
| 8,491,153 | B2 | 7/2013 | Maxik |
| 8,506,612 | B2 | 8/2013 | Ashdown |
| 9,715,242 | B2 | 7/2017 | Pillai et al. |
| 2009/0281604 | A1* | 11/2009 | De Boer ............ H05B 45/20 607/88 |
| 2010/0063566 | A1* | 3/2010 | Uchiumi ............ A61M 21/00 607/89 |
| 2010/0174345 | A1 | 7/2010 | Ashdown |
| 2010/0244740 | A1 | 9/2010 | Alpert et al. |
| 2011/0037378 | A1 | 2/2011 | Yagi et al. |
| 2011/0299277 | A1 | 12/2011 | Ehara |
| 2012/0068608 | A1 | 3/2012 | Covaro et al. |
| 2012/0069551 | A1 | 3/2012 | Bues et al. |
| 2012/0206050 | A1 | 8/2012 | Spero |
| 2013/0293150 | A1 | 11/2013 | Maxik et al. |
| 2015/0062892 | A1 | 3/2015 | Krames et al. |
| 2016/0128158 | A1 | 5/2016 | Harder |
| 2016/0262222 | A1* | 9/2016 | Frohnapfel ............ H05B 45/20 |
| 2018/0056027 | A1* | 3/2018 | Peeters ............ A61N 5/0618 |

FOREIGN PATENT DOCUMENTS

| | | |
|---|---|---|
| CN | 104685428 A | 6/2015 |
| DE | 102013221723 A1 | 4/2015 |
| EP | 2094064 A1 | 8/2009 |
| KR | 1020150026968 A | 3/2015 |
| WO | 20080146219 A1 | 12/2008 |
| WO | 2013151661 A1 | 10/2013 |
| WO | 2014189945 A1 | 11/2014 |
| WO | 2015014936 A1 | 2/2015 |
| WO | 2015052207 A1 | 4/2015 |
| WO | 2015059136 A1 | 4/2015 |
| WO | 2015200730 A1 | 12/2015 |

OTHER PUBLICATIONS

George Kelly, "Understand Color Science to Maximize Success with LEDs", LEDs Magazine, 7 pgs, Appendix J, http://www.ledsmagazine.com/articles/2012/05/understand-color-science-to-maximize-success-with-leds-magazine,html, accessed by applicant on Dec. 17, 2015.

Musco Corporation, PCT/US2016/067340 filed Dec. 16, 2016, "International Search Report and Written Opinion of the International Searching Authority", dated May 30, 2017.

Google Patents translation of DE 102013221723 A1, accessed on Sep. 18, 2017.

Cree Technical Article, "LED Color Mixing: Basics and Background", CLD-AP38 Rev 1B, 23 pages 2015.

U.S. Appl. No. 14/955,378, 21 pages, filed Dec. 1, 2015.

U.S. Appl. No. 62/345,559, 21 pages, filed Jun. 3, 2016.

U.S. Appl. No. 15/382,232, 66 pages, filed Dec. 16, 2016.

PCT Serial No. PCT/US16/67340, 66 pages, filed Dec. 16, 2016.

Berman, "New Discoveries in Vision Affect Lighting Practice", Lawrence Berkeley National Laboratory, 8 pages (2012).

Horiguchi, et al., "Human Trichromacy Revisited", PNAS, 10 pages (2012).

DW, Made for Minds, "Intelligent Light", 2 pages (2016), (http://www.dw.com/en/intelligent-light/av-19112290), last accessed on Jun. 14, 2017.

Lewin, Ian, "Lamp Color and Visibility in Outdoor Lighting Design", Lighting Sciences Inc., 14 pages (1999).

Lucas, et al., "Measuring and Using Light in the Melanopsin Age", Trends in Neurosciences, vol. 37, No. 1, 9 pages (2014).

Email Re: Priorities IP-1410 (circadian lighting), 1 page (2016).

Schlesselman, et al., "Brightness matching determines the trade-off between S/P values and illuminance level", Musco Sports Lighting, LLC, 16 pages (2015).

Schlesselman, et al., "Brightness judgments in a simulated sports field correlate with the S/P value of light sources", Musco Sports Lighting, LLC, 18 pages (2015).

Spitschan, et al., "Opponent melanopsin and S-cone signals in the human pupillary light response", PNAS, vol. 111, No. 43, 5 pages (2014).

Vienot, et al., "Domain of metamers exciting intrinsically photosensitive retinal ganglion cells (ipRGCs) and rods", Journal of the Optical Society of America A, vol. 29, No. 2, 12 pages (2012).

Musco Corporation, "Notification of the First Office Action", in connection with Chinese Patent App. No. 201780034417.1, filed Jun. 1, 2017, 6 pages, Date of Notification Sep. 11, 2019.

European Patent Office, EP17807499.3, "Extended European Search Report" 8 pages, dated Jan. 2, 2020.

\* cited by examiner

Existing Art

Existing Art

Existing Art

| Spectrum Name | Photopic Lumens | Scotopic Lumens | Melanopic Lumens | S/P Ratio | M/P Ratio 2011 | M/P Ratio 2014 | CIE x | CIE y | CCT | duv | CRI | TM-30 Rf | TM-30 Rg | TLCI 2012 Qa |
|---|---|---|---|---|---|---|---|---|---|---|---|---|---|---|
| 510 | 9765.5 | 40841.3 | 85659.7 | 4.18 | 8.7717 | 1.7324 | 0.0722 | 0.7159 | | 0.1843 | .0 | NaN | NaN | .0 |
| 520 | 12631.2 | 37906.6 | 69940.6 | 3.00 | 5.5371 | 1.0936 | 0.1275 | 0.7762 | | 0.1743 | .0 | NaN | NaN | .0 |
| 530 | 14927.3 | 32794.5 | 52673.2 | 2.20 | 3.5267 | .6969 | 0.1951 | 0.7630 | | 0.1552 | .0 | NaN | NaN | .0 |
| 540 | 16359.7 | 26418.7 | 38527.7 | 1.61 | 2.2328 | .4410 | 0.2840 | 0.7179 | | 0.1310 | .0 | NaN | NaN | .0 |
| 550 | 18944.6 | 19812.0 | 23236.6 | 1.17 | 1.3713 | .2708 | 0.3318 | 0.6606 | | 0.1030 | .0 | NaN | NaN | .0 |
| 560 | 16770.1 | 13828.5 | 13508.3 | .82 | .805 | .1591 | 0.3984 | 0.5983 | | 0.0720 | .0 | NaN | NaN | .0 |
| 570 | 15906.6 | 8984.4 | 7186.1 | .56 | .4518 | .0892 | 0.4629 | 0.5355 | 3454 | 0.0412 | -28.7 | .1 | .1 | 1.1 |
| 580 | 14451.4 | 5436.6 | 3533.7 | .38 | .2445 | .0483 | 0.5235 | 0.4756 | 2413 | 0.0178 | -24.9 | .1 | .0 | 1.1 |
| 590 | 12568.4 | 3070.4 | 1635.0 | .24 | .1301 | .0257 | 0.5778 | 0.4216 | 1688 | 0.0059 | -22.2 | .2 | .0 | 1.2 |
| 600 | 10467.9 | 1627.3 | 726.5 | .16 | .0694 | .0137 | 0.6232 | 0.3764 | 1246 | 0.0017 | -8.0 | 1.0 | .0 | 1.4 |
| 610 | 8335.0 | 816.5 | 316.3 | .10 | .0379 | .0075 | 0.6583 | 0.3414 | | 0.0000 | .0 | .0 | .0 | .0 |
| 620 | 6303.8 | 391.9 | 137.1 | .06 | .0218 | .0043 | 0.6837 | 0.3161 | | 0.0000 | .0 | .0 | .0 | .0 |
| 630 | 4488.9 | 182.1 | 59.9 | .04 | .0134 | .0026 | 0.7013 | 0.2986 | | 0.0000 | .0 | .0 | .0 | .0 |
| Melanopic Curve | 20142.6 | 108192.2 | 266801.2 | 5.37 | 13.2456 | 2.6161 | 0.1347 | 0.2805 | | 0.0000 | .0 | .0 | .0 | .0 |
| User Input MP Metamer | 71669.7 | 245050.6 | 608358.5 | 3.42 | 8.5002 | 1.6788 | 0.2806 | 0.2883 | | 0.0000 | 66.1 | 64.7 | 88.7 | 51.6 |

Figure 3C

Calculation Point

Chromaticity Coordinates

Abscissa | Ordinate
--- | ---
0.28063 | 0.28829

Standard Observer
- ● 2°: CIE 1931
- ○ 10°: CIE 1964
- ○ 2°: CIE 2006
- ○ 10°: CIE 2006
- ○ 10°: CIE 2006 LMS Cone Space of Primaries Used
- ● Maximum
- ○ Medium
- ○ Minimum

Desired S/P Ratio
- ● Maximum
- ○ Minimum
- ○ Max & Min
- ○ User Input

[ Find S/P Ratio(s) ]

Desired M/P Ratio
- ○ Maximum
- ○ Minimum
- ○ Max & Min
- ● User Input 8.5

[ Find M/P Ratio(s) ]

LED X 84 (7 X 12 Array)
(Subset 1=42 high M/P LEDs)
(Subset 2=42 low M/P LEDs)

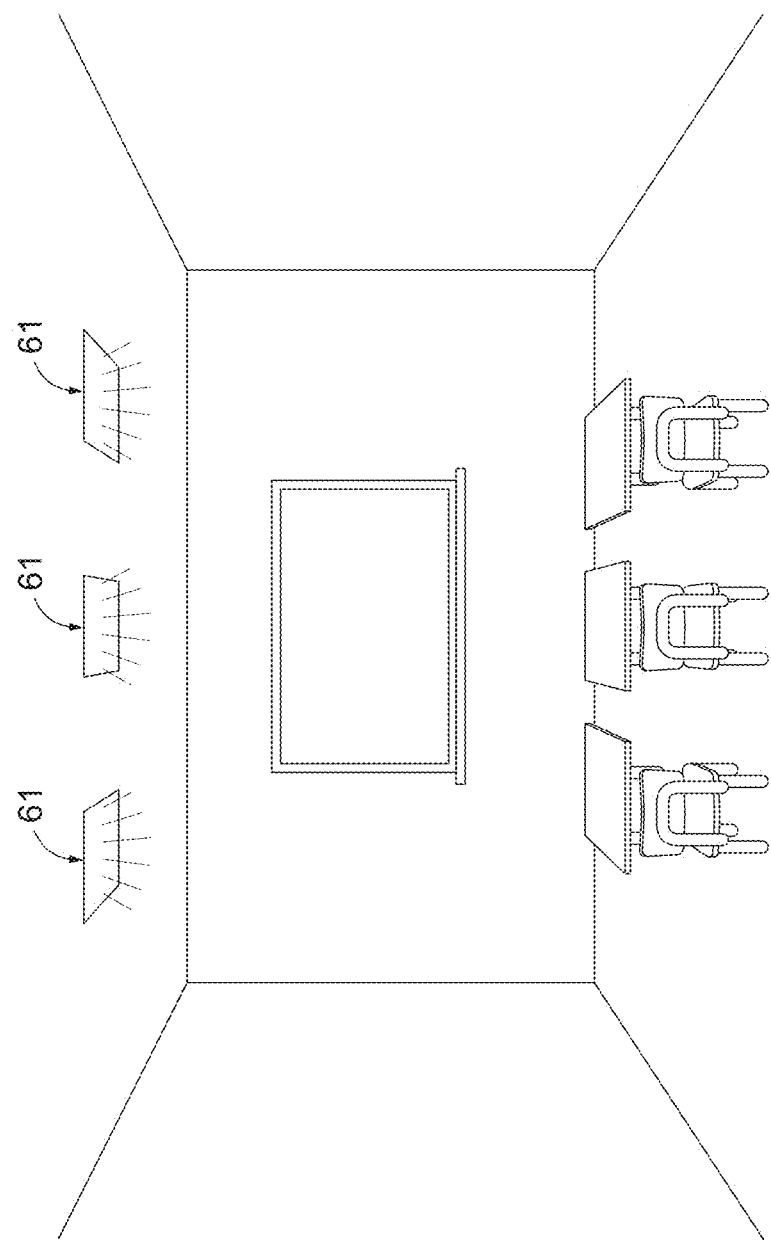

| Spectrum Name | Photopic Lumens | Scotopic Lumens | Melanopic Lumens | S/P Ratio | M/P Ratio 2011 | M/P Ratio 2014 | CIE x | CIE y | CCT | duv | CRI | CRI R9 | TM-30 Rf | TM-30 Rg | TLCI 2012 Qa |
|---|---|---|---|---|---|---|---|---|---|---|---|---|---|---|---|
| Melanopic Sensitivity Function | 19323.8 | 107316.0 | 267619.1 | 5.55 | 13.5492 | 2.7153 | 0.1339 | 0.2669 | | 0.0000 | | | | | |
| 5700K 80 CRI LED | 10654.2 | 21433.1 | 45892.1 | 2.01 | 4.3074 | .8507 | 0.3259 | 0.3318 | 5762 | 0.0023 | 81 | 1.2 | 77 | 99 | 6.7 |

Figure 6B

Cross sectional view of simulated sports field and lighting layout. Observer is positioned looking at field simulation with 4' eye height achieved by adjustable height chair.

Floor, chair and lit platform, perspective view from right hand side of platform Drawing of the ETC fixture CIE Diagram of the seven LED sources and the resultant metamers

APPARATUS, METHOD, AND SYSTEM FOR PROVIDING TUNABLE CIRCADIAN LIGHTING AT CONSTANT PERCEIVED BRIGHTNESS AND COLOR

CROSS-REFERENCE TO RELATED APPLICATIONS

This application claims the benefit under 35 U.S.C. 119 and/or 120 of and priority to U.S. Provisional Application Ser. No. 62/345,559, filed Jun. 3, 2016, which is incorporated by reference in its entirety herein.

I. BACKGROUND OF THE INVENTION

The present invention generally relates to adjusting lighting source output to provide a biological/physiological benefit to a user in accordance with desired circadian stimulation. More specifically, the present invention relates to improvements in so-called circadian lighting (also referred to as "bio lighting" or "photobiology" or "light therapy") insomuch that shifts in operational variables in the light source output which produce said biological/physiological benefits—namely, dynamic shifts in the melanopic content of the light which impacts, among other things, alertness and also (i) do not result in a perceivably different color of ambient or background light over the course of operation and (ii) do not necessarily maintain a constant luminance or illuminance but rather can maintain a constant perceived ambient or background brightness.

Over the last few decades great effort has been spent trying to understand what will be referred to herein as the human response to lighting. A human response to lighting can be immediate and physical—like squinting in the presence of a light source which produces glare—or slower to evolve and more visceral—like a diminishing effect due to seasonal affective disorder (SAD) over prolonged exposure to appropriate light therapy. Research has led to a widely accepted truth: lighting does more than just illuminate, and the eyes do more than just see. More specifically, lighting does more than facilitate vision—it has a biological/physiological impact on the viewer.

To quantify circadian effects, a number approaches have been taken. Melatonin, the active and causal hormone, has been measured in subjects and correlated to circadian behavior which, in turn, has been correlated to, among other conditions, alertness. Experimenters have adjusted intensity and exposure to light in an attempt to yield one or more biological/physiological benefits (such as perceived or measured alertness); see, for example, U.S. Pat. Nos. 8,028,706 and 8,506,612 both of which are incorporated by reference herein in their entirety. Experimenters have adjusted spectral power distribution (SPD) via selection of colored light sources such as LEDs to encourage melatonin production/metabolization or otherwise regulate circadian rhythms (see again U.S. Pat. No. 8,506,612). Experimenters have even adjusted the SPD of a light source comprised of multiple colored LEDs by timed power or duty cycle adjustments to said LEDs in accordance with anticipated circadian rhythms. These efforts can produce a beneficial circadian lighting product, but they suffer from a few deficiencies.

Commercially available circadian lighting systems produce a "colder" bluish light during the day to initiate greater circadian stimulation and a "warmer" reddish light during the evening to diminish said stimulation. The bluish light (i.e., the colder light generally associated with higher correlated color temperatures (CCTs)) is well known to be more effective at suppressing melatonin. However, these commercially available lighting systems are perceivably bluer during the day and perceivably redder in the evening such that there is a prominent and noticeable color shift and as well an overall perceived brightness shift during the operation time. This is perhaps one of the reasons why many commercially available circadian lighting systems are sold as individual units such that they may be independently switched on and off as needed to produce the desired biological/physiological benefit, much like how one switches on a nightlight only in the evening. The prominent color shift makes state-of-the-art circadian lighting systems less suitable for general purpose lighting that requires good color rendering for a task performed thereunder; further it may be annoying or bothersome due to the visible color shifting, especially for computer monitors and other personal electronic devices where background lighting surrounding the visual task is prominent. So, often times, any circadian lighting system must either be paired with general lighting, or must be operated in an "either/or" mode such that it is operated either as general purpose lighting or in a special mode that provides biological/physiological benefits (see again U.S. Pat. No. 8,506,612). This can be cumbersome and annoying as well as not cost-effective for a user.

Some advancements have been made insomuch that under some conditions the light produced in the "awake" (i.e., colder, bluer) mode is much closer in perceivable color to the "sleep" (i.e., warmer, redder) mode (see U.S. Pat. No. 8,378,574 incorporated by reference herein in its entirety) but the shift remains perceivable even when the light is perceivably white and illuminance is constant. Furthermore, when the illuminance is held constant the perceived brightness of such illumination will be observed as changing. This brightness phenomenon has been reported extensively in lighting engineering literature and is now attributed to responses of the recently discovered melanopsin retinal photo receptor—such having been found to be efficiently stimulated by bluer-rich lighting.

The preceding poses a problem: state-of-the-art circadian lighting systems rely upon adding blue light for an "awake" mode, and transition to reducing blue and adding redder light for a "sleep" mode; even systems employing "white" sources typically include many RGB-type LEDs heavy in red or blue light. Therefore, if one adjusts the SPD of the sources so to change the color temperature of the light source (e.g., transitioning from colder light to warmer light), even if one keeps illuminance constant, a user will likely perceive a shift in color and brightness, wherein the perceived shift in brightness is due to the response of melanopsin receptors which are not accounted for in the calibration of standard light meters. Therefore, using state-of-the-art techniques it is not possible to produce a circadian lighting system of perceivably constant brightness and color. Thus, there is room for improvement in the art.

II. SUMMARY OF THE INVENTION

State-of-the-art circadian lighting systems produce desirable biological or physiological effects when transitioning from a colder bluish light to a warmer reddish light in accordance with a desired circadian entrainment. However, these effects have concomitant effects that are not considered desirable. Often, said circadian lighting systems are not suitable for general purpose lighting since the perceived color of the lighting on the whole is affected, as well as affecting specific tasks which require assessment of color, and so these must be supplemented with additional lighting.

Alternatively, said systems can be operated in a general purpose task lighting mode, but not at the same time as providing said biological/physiological effects, or if operated at the same time they do not provide perceivably constant brightness. In the former scenario, additional cost is incurred by the user, and in the latter scenario adverse biological/physiological effects (e.g., distraction from task) could be sustained as a result of the changing perceived brightness.

Attempts have been made to incorporate circadian active background lighting for electronic devices such as monitors, tablets and cell phones. Desired circadian activity is presently produced by varying the color and brightness of the device background lighting, but again is noticeable annoying and therefore less desirable than the present invention.

It is therefore a principle object, feature, advantage, or aspect of the present invention to improve over the state of the art and/or address problems, issues, or deficiencies in the art.

Technical research reports recently presented at the national conference of the Illuminating Engineering Society (November 2015) by Schlesselman, et al discussed findings relating to concepts of brightness, melanopsin receptors, melanopic content and widely known S/P (scotopic-to-photopic) ratios, etc. relevant to the current invention. These reports are Schlesselman et al, *Brightness judgments in a simulated sports field correlate with the S/P value of light sources* (hereinafter individually "IES1" and included later in this description); and Schlesselman et al, *Brightness matching determines the trade-off between S/P values and illuminance level*, (hereinafter individually "IES2" and included later in this description) (hereinafter sometimes cited collectively as simply "Schlesselman et al") which are included for reference below in their entireties. In those reports the more familiar S/P ratio was used as the highly correlated proxy for relative melanopsin content (M/P value) of the viewed illumination. Said research presented has demonstrated that it is not necessarily the blue content or even correlated color temperature (CCT) of light that triggers melanopsin receptors associated with non-visual biological/physiological input with respect to circadian entrainment, but rather the melanopic content quantified by the melanopic/photopic (M/P) ratio (see below) of the SPD of light. As such, a primary aspect of the present invention is to provide the benefits of traditional circadian lighting without having to rely heavily upon observable color changes provided by the singular use of blue and red auxiliary lighting that produce the different colored and circadian active light.

It was further discovered by vision scientists that melanopsin receptors are absent in the central fovea of the eye, but rather are distributed throughout the remaining retinal body—which implies such receptors are not of concern for perceived object brightness (i.e., brightness of a centrally viewed object wholly confined to 2 degrees or less of visual field), but these melanopsin receptors, as shown in Schlesselman et al., are essential for quantifying background brightness (i.e., the brightness of the overall space rather than the object). As such, a primary aspect of the present invention is to provide benefits of traditional circadian lighting while moving away from state-of-the-art approaches which emphasize object brightness (e.g., by considering only object luminance) as a control variable in favor of the biologically effective background brightness.

Further objects, features, advantages, or aspects of the present invention may include one or more of the following:

a. in terms of perceived color of background lighting, to provide an imperceptible shift in color from lighting with a high melanopic content to a low melanopic content or vice versa;

b. to provide said biologically effective lighting at a variety of nominal color temperatures so as to, e.g., accommodate a number of tasks and/or environments; and c. to provide said shift at a constant perceived spatial or background brightness even though their measured traditional illuminance varies.

A method according to one aspect of the present invention comprises employing a single light fixture, module, luminaire, or light source set to provide both general purpose or background lighting and circadian lighting, wherein the light source includes a first subset of sources such as LEDs with a high melanopic content and a second subset of sources such as LEDs with a low melanopic content of identical color (metameric lights) and wherein the method comprises transitioning together in mixed concert from the first subset of sources or LEDs to the second subset of sources or LEDs according to a predetermined profile. A further method according to aspects of the present invention comprises having said high melanopic content have a relatively high percentage of energy in the band around 488 nm, such as e.g. about 0.40 relative energy normalized to 1.0; further e.g. where relative power is on the order of 0.20 between 478 to 498 nm, on the order of 0.30 between 483 to 493 nm, and on the order of 0.40 between 486 to 490 nm, as well as other values that may be derived from the examples of SPD included herein or as may be appropriately developed.

An apparatus according to one aspect of the present invention comprises an LED lighting fixture including said first and second subsets of LEDs adapted and controlled to provide both general purpose and circadian lighting.

A system according to one aspect of the present invention comprises the aforementioned method in combination with the aforementioned apparatus to produce an LED lighting system that provides biological/physiological operational benefits while also providing general illumination, and in a manner that does not produce perceivably variable brightness or color.

These and other objects, features, advantages, or aspects of this application of the present invention will become more apparent with reference to the accompanying specification and claims.

III. BRIEF DESCRIPTION OF THE DRAWINGS

From time-to-time in this description reference will be taken to the drawings which are identified by figure number and are summarized below.

Figure 3A:
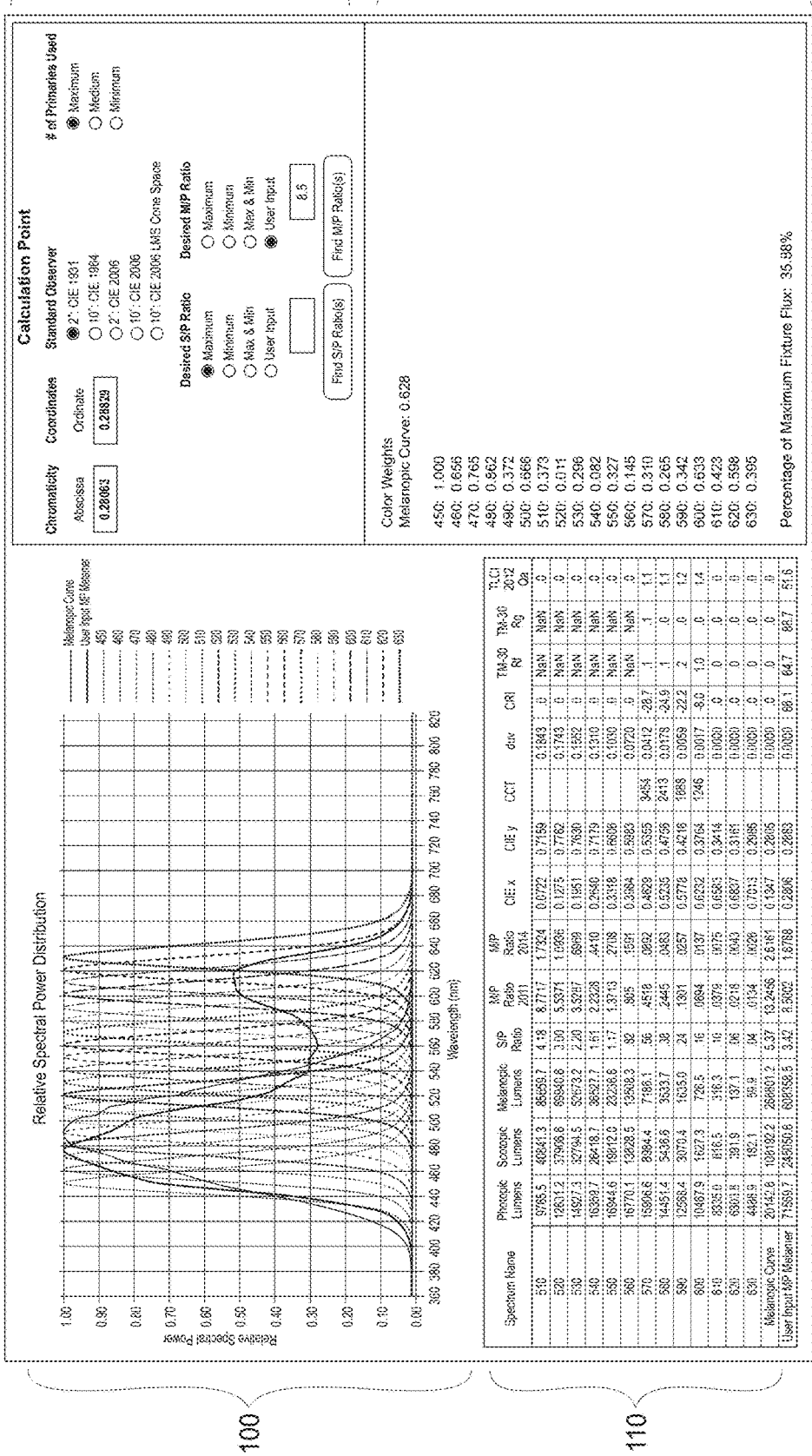
FIG. 3A shows a computer graphic screen capture from a calculation software application for use in the method of FIG. 2.
Figure 3B:
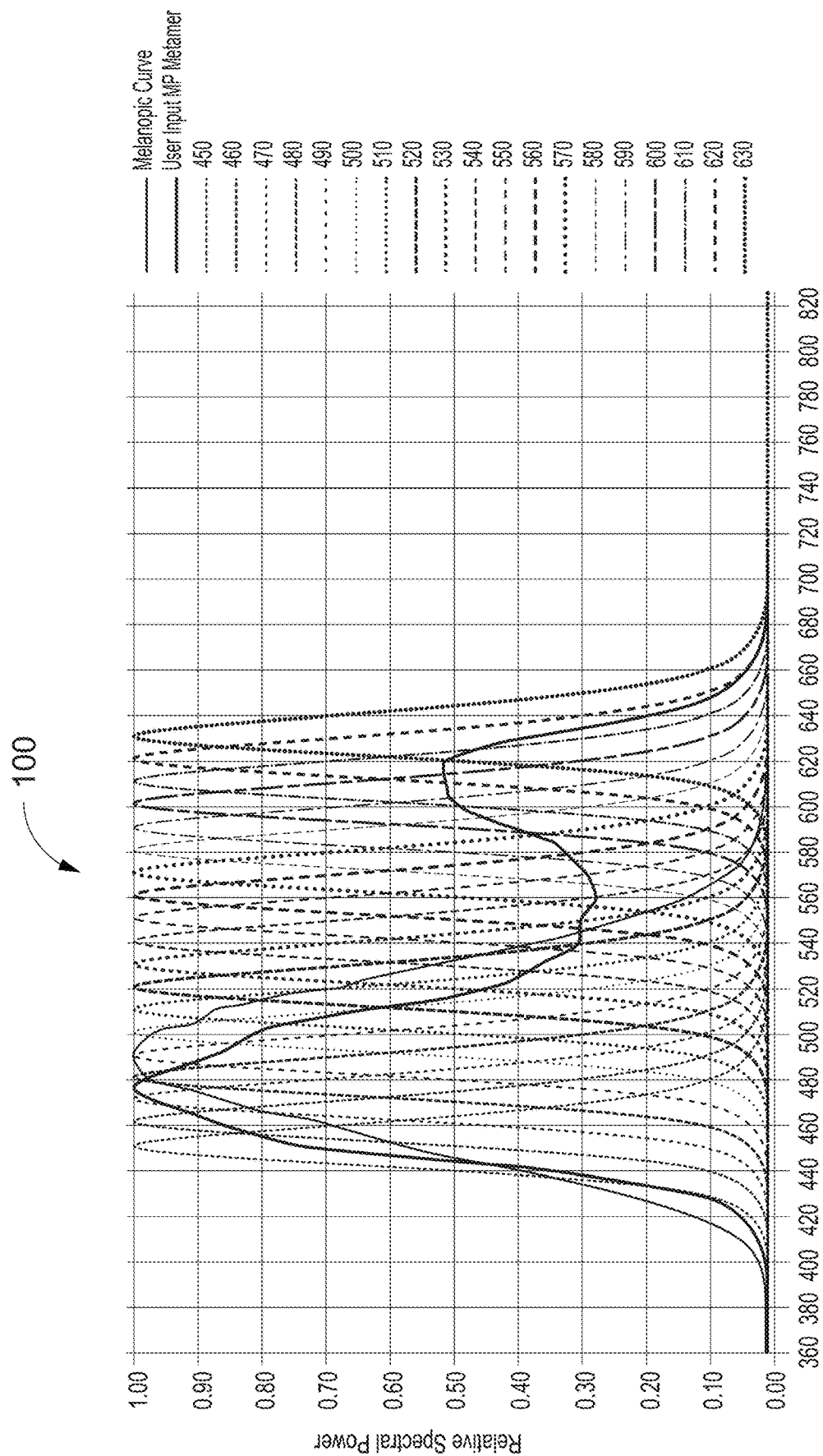
Figure 3D:
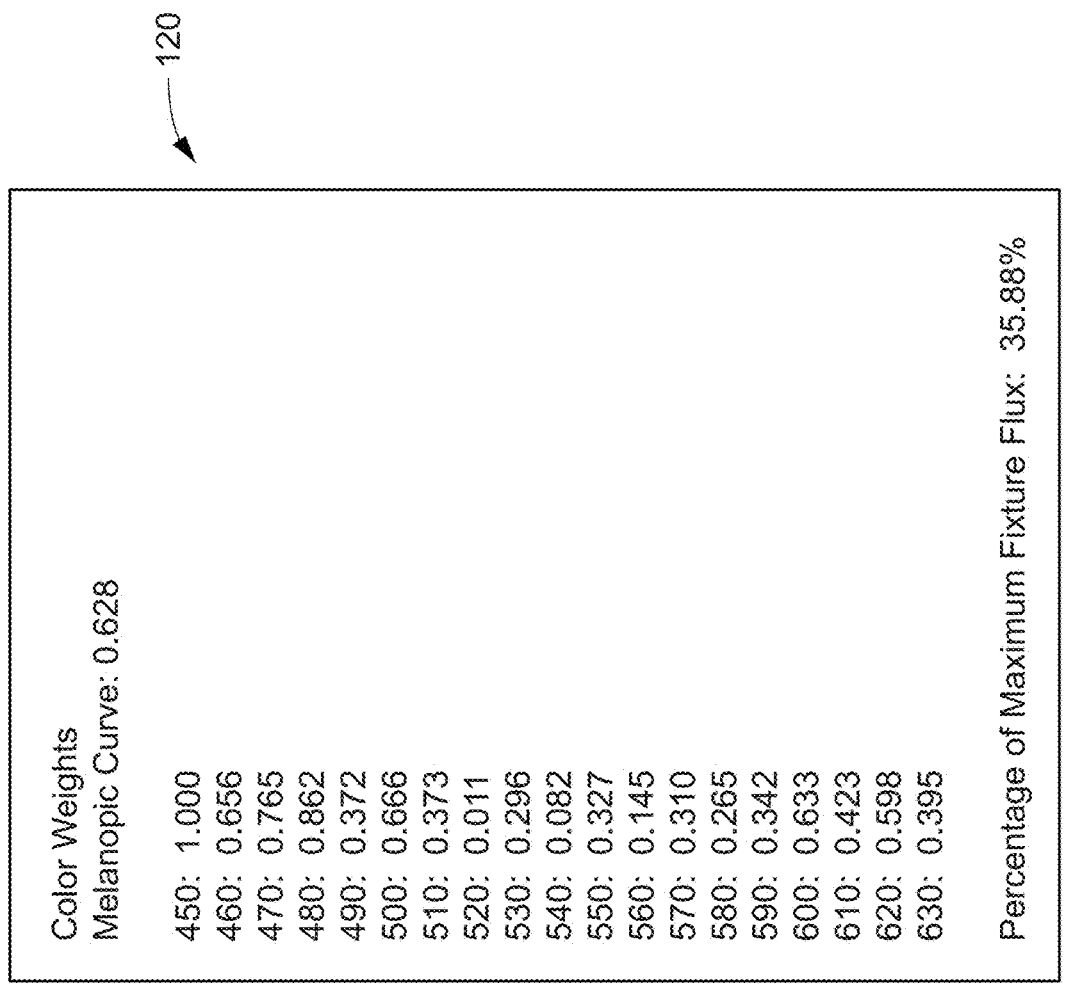

FIGS. 3B-E are renderings of the graphic of FIG. 3A illustrating areas 100, 110, 120, and 130 of the image of FIG. 3A in order to provide clear understanding of its content.

Figure 4A:
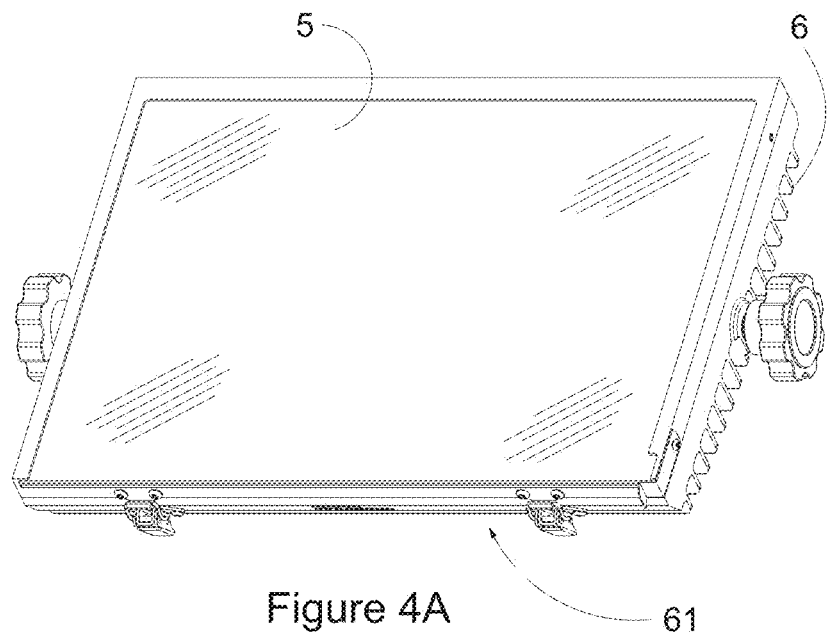
Figure 4B:
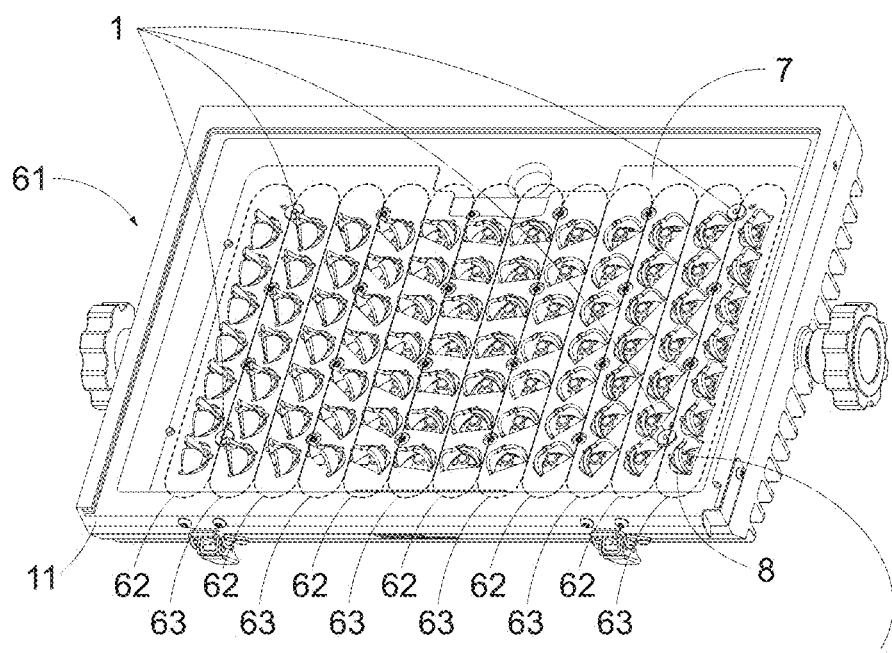

FIGS. 4A and B illustrate one possible LED lighting fixture according to aspects of the present invention. For illustrative purposes only, FIG. 4A illustrates a light transmissive external lens 5 by graphic symbol and without showing the LED sources behind it, but FIG. 4B shows how those LEDs would normally appear to a viewer including with the lens in place.

FIGS. 5A-D illustrate various possible apparatuses and scenarios in which the LED lighting fixture of FIGS. 4A and B may be employed to provide general purpose and circadian lighting according to aspects of the present invention; note that for clarity the external lens is illustrated with graphic symbol indicating light transmissivity.

Figure 6A:
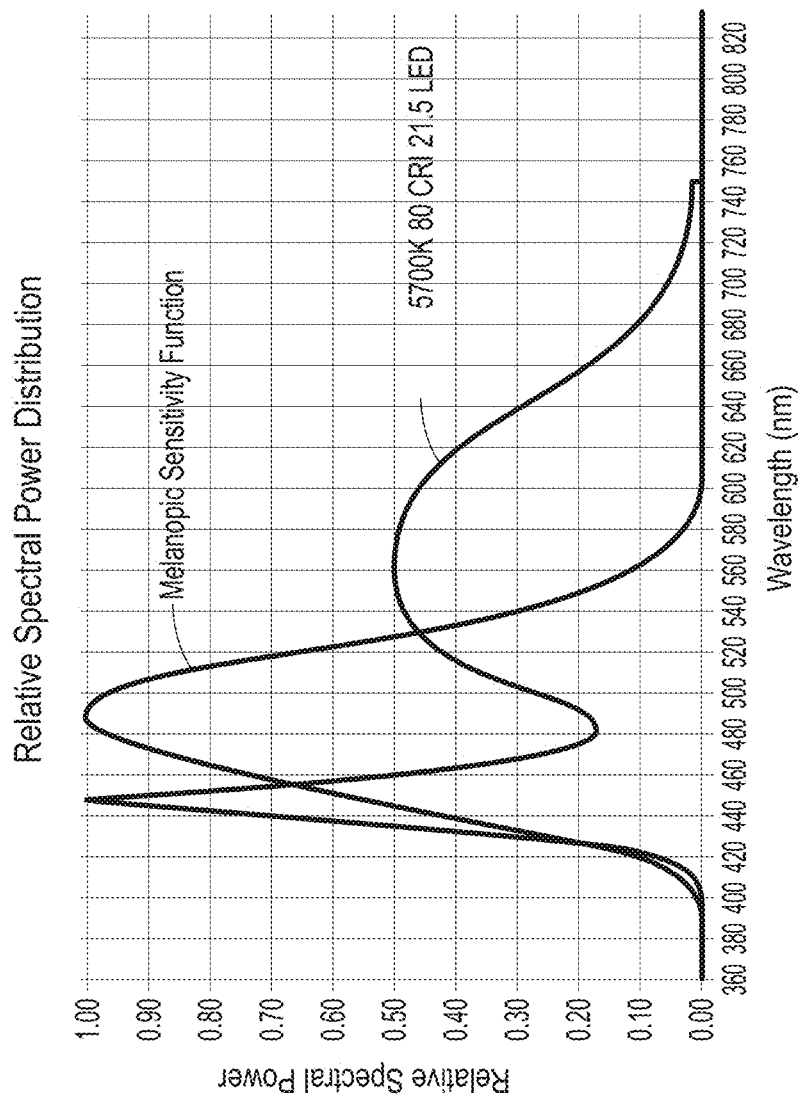

FIG. 6A illustrates the melanopic spectral sensitivity function overlaid with a SPD of a typical prior art white LED.

FIG. 6B is a table providing information about the spectral functions represented in FIG. 6A.

Figure 7:
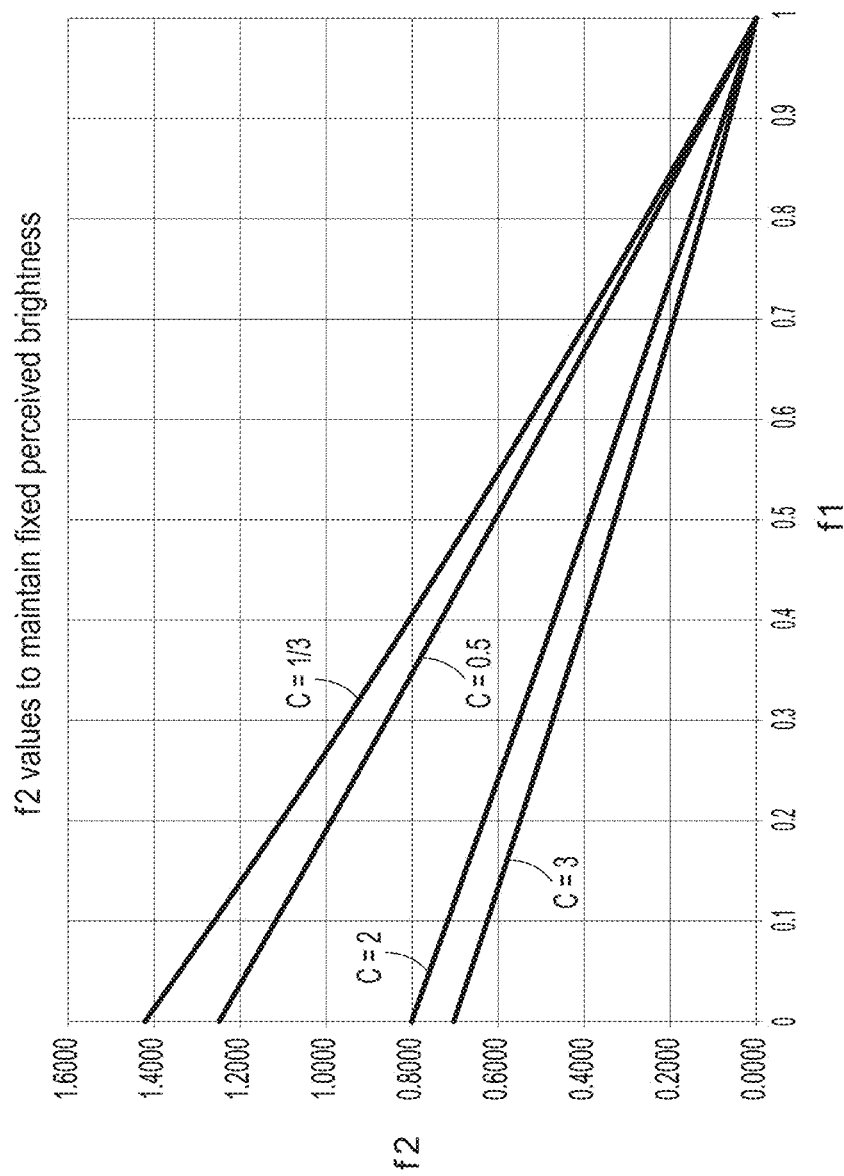

FIG. 7 is a graph showing the relationship between the light level values applied to regulate two different light sources used in a lighting system according to aspects of the invention.

Figure 8A:
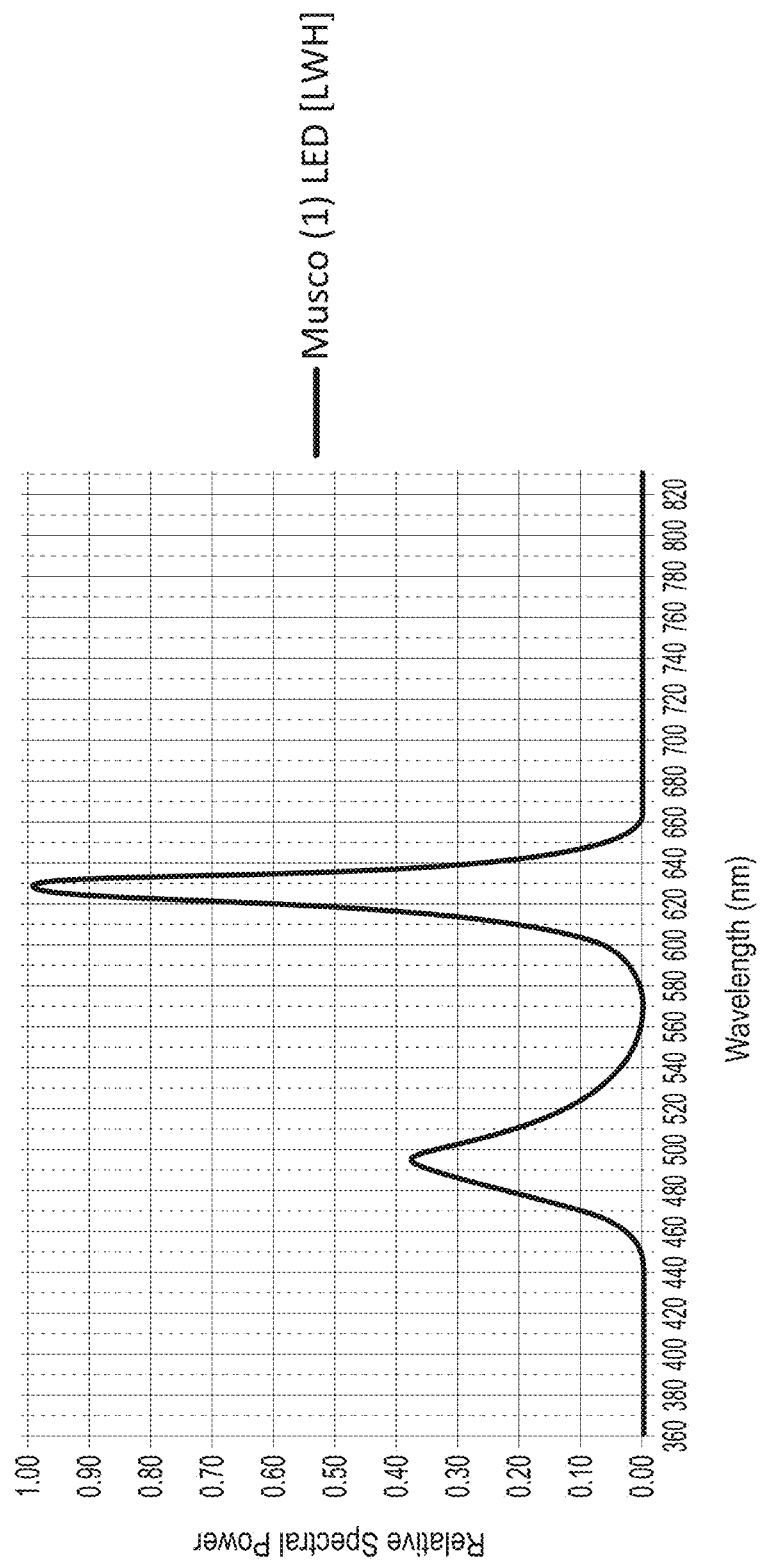
Figure 9:
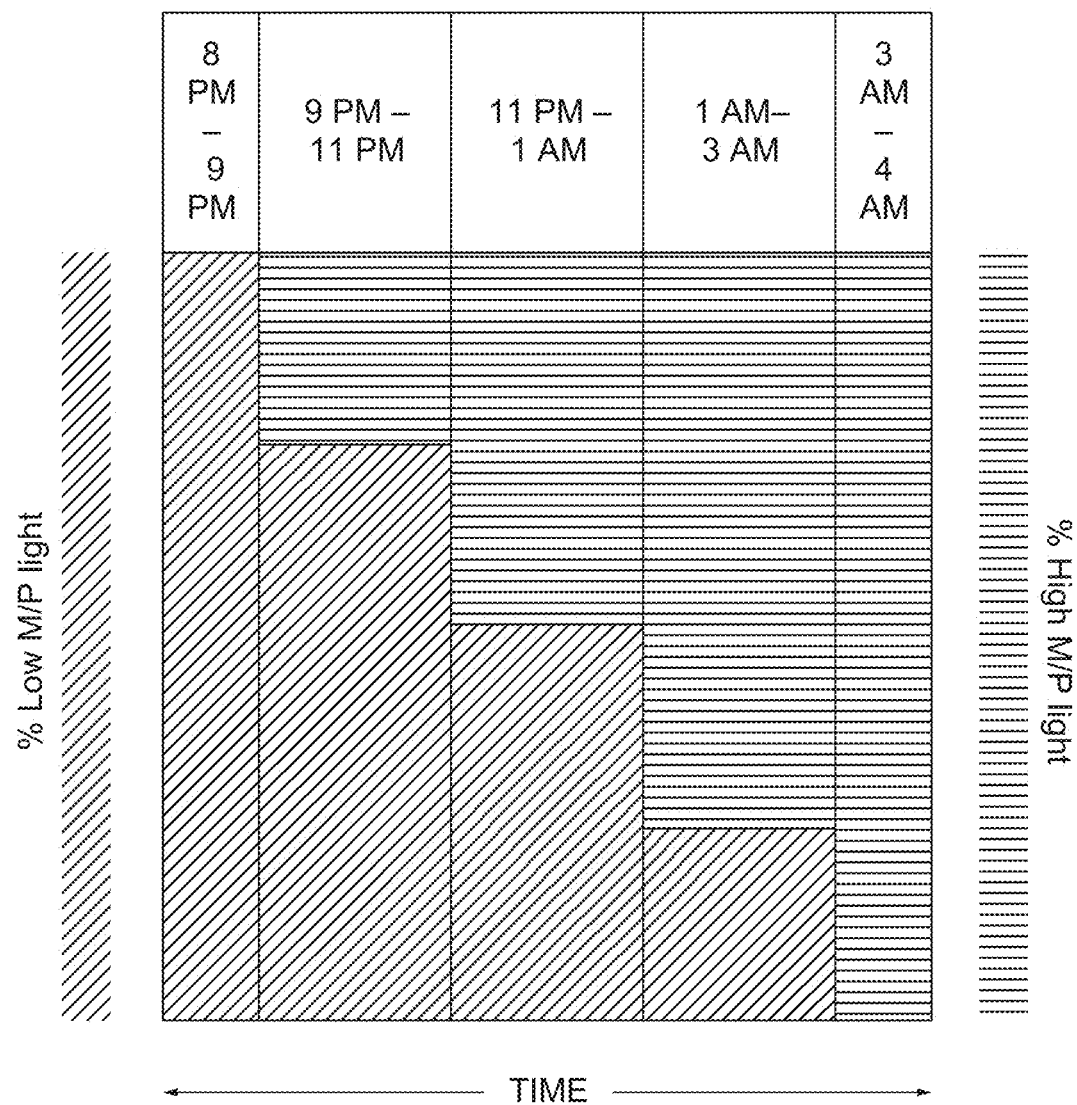

FIGS. 8A and B are graphs showing SPD for metamers having high melanopic content according to aspects of the invention FIG. 9 is a graphic representation of an operational profile for lighting showing a transition from low M/P lighting to high M/P lighting over time according to aspects of the invention.

FIGS. 10A-I are illustrations and graphs referred to in the IES #1 and IES #2 sections infra.

IV. DETAILED DESCRIPTION OF EXEMPLARY EMBODIMENTS

A. Overview

To further an understanding of the present invention, specific exemplary embodiments according to the present invention will be described in detail. Frequent mention will be made in this description to the drawings. Reference numbers will be used to indicate certain parts in the drawings. Unless otherwise stated, the same reference numbers will be used to indicate the same parts throughout the drawings.

Regarding terminology, reference has been given herein to biological and/or physiological benefits associated with lighting; particularly, circadian lighting. These benefits are widely accepted as realized (as opposed to theoretical)—the use of the terms "biological" and "physiological" are not intended to purport any particular benefit as being more realized than another, nor meant to disparage any particular benefit not widely accepted as being realized. The aforementioned terms are used generically to describe benefits that might be achieved by light induced circadian entrainment, and more broadly, non-visual responses to lighting that may relate to circadian lighting.

Further regarding terminology, reference has been given herein to general purpose lighting and tasks that might be performed thereunder. While some specific examples are given, the use of the terms "general" and "task" are not intended to limit the use or scope of the invention. General purpose lighting could be exterior or interior lighting, with or without a specific task in mind. The use of "general purpose" is also intended to provide a cue with respect to perceived brightness; specifically, that aspects according to the present invention are directed to background brightness rather than object brightness (e.g., object luminance), and so one is directed to consider the overall purpose and environment of the lighting rather than primarily the color or brightness of an object in one's central view. Whereas in the prior art—including some of the sources included herein as references—brightness is a term used colloquially and interchangeably with luminance, this is not the definition of "brightness" as used herein. Conceptually this can be likened to an electronic device such as a tablet computer, phone, or gaming device. Whereas prior art is describing brightness with respect to a central object (e.g., how bright the letters on a tablet appear), the present invention is describing brightness with respect to everything outside of the central focus (e.g., how bright the background on the tablet computer appears). While this may appear to be a relatively small difference, it should be noted that the effects of the melanopsin receptor are nascent and this new approach to lighting design deserving of such delineation. And so to avoid confusion, care has been given to use the terms "illuminance," "luminance," and "perceived brightness" in accordance with their widely accepted definitions within the lighting industry, and barring that, in accordance with Schlesselman et al.

Further regarding terminology, reference is given herein to "perceived color"; namely, color that is perceived by the human eye to be the same, regardless of whether it is produced by the same specific detailed spectrum producing the light. As is described herein, the invention makes use of metamerism; specifically, taking advantage of the human visual response (i.e., the cones of the eye responding broadly to SPD rather than at every possible visual wavelength). As is well known in vision science and in the art of lighting, it is widely understood that humans have three types of cones which are responsible for initiating color perception (one cone type each euphemistically referred to as red, green, and blue cones) resulting in a characterization of a perceived color in terms of neural computation based on the outputs of said cones. As used herein, two sources characterized as having the same "perceived color" are merely two sources which produce the same overall stimulation of each of the three cones and therefore perceived color, regardless of whether the source specific spectral power distributions (SPDs) are identical.

Lastly regarding terminology, reference is given herein to "melanopic content" as well as the relative melanopic content or melanopic/photopic (M/P) value of the spectral power distribution of a light source. While one or more visuals are later provided, to give further definition to this term, one may consider melanopic content for a light source of a given SPD as M, where M is determined by convolving said SPD with a melanopic sensitivity function (later described, also see FIG. 6A) which has been normalized by a numerical value applied either (a) at its peak wavelength (such as unity) or (b) to a numerical value of 683 applied at the wavelength of 555 nanometers consistent with the traditional normalization of the photopic sensitivity function. M/P is then determined by subsequently dividing that convolution by the lumens associated with the same SPD. The result is a value obtained in either effective milliwatts per lumen (mW/lm) for the unity normalization or in the latter case a dimensionless homogeneous number (i.e. melanopic lumens per photopic lumen). In either case there is a fixed numerical conversion for all sources between these normalizations or any other considered although the specific conversion factor will depend on normalization choice. It should also be noted that application of the invention herein described is not limited to any specific normalization procedure.

As described herein, a high melanopic content light source would have a higher M/P value and a low melanopic content light source would have a lower M/P value when compared to one another; further it should be noted that because this measure is a ratio (M/P) it is independent of net light intensity. Thus, when reference is given herein to "tuning" a light source, one is merely changing the duty cycle or power input to LEDs (or other light sources) having different M/P values but with a specific profile to maintain color and perceived brightness. Additional information regarding the measurement of perceived brightness and melanopic/scotopic/photopic functions may be found in Schlesselman et al.

Figure 1A:
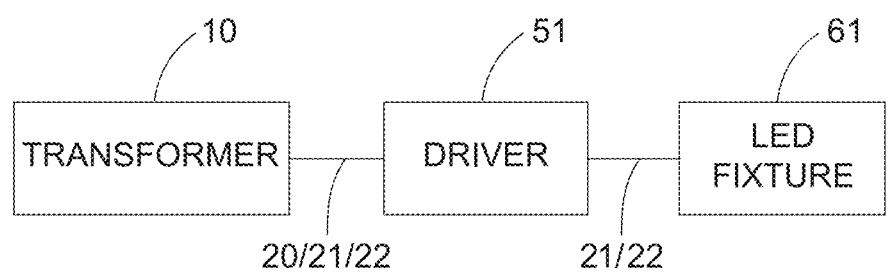
FIG. 1A illustrates a simple lighting system according to existing art in block diagram form.
Figure 1B:
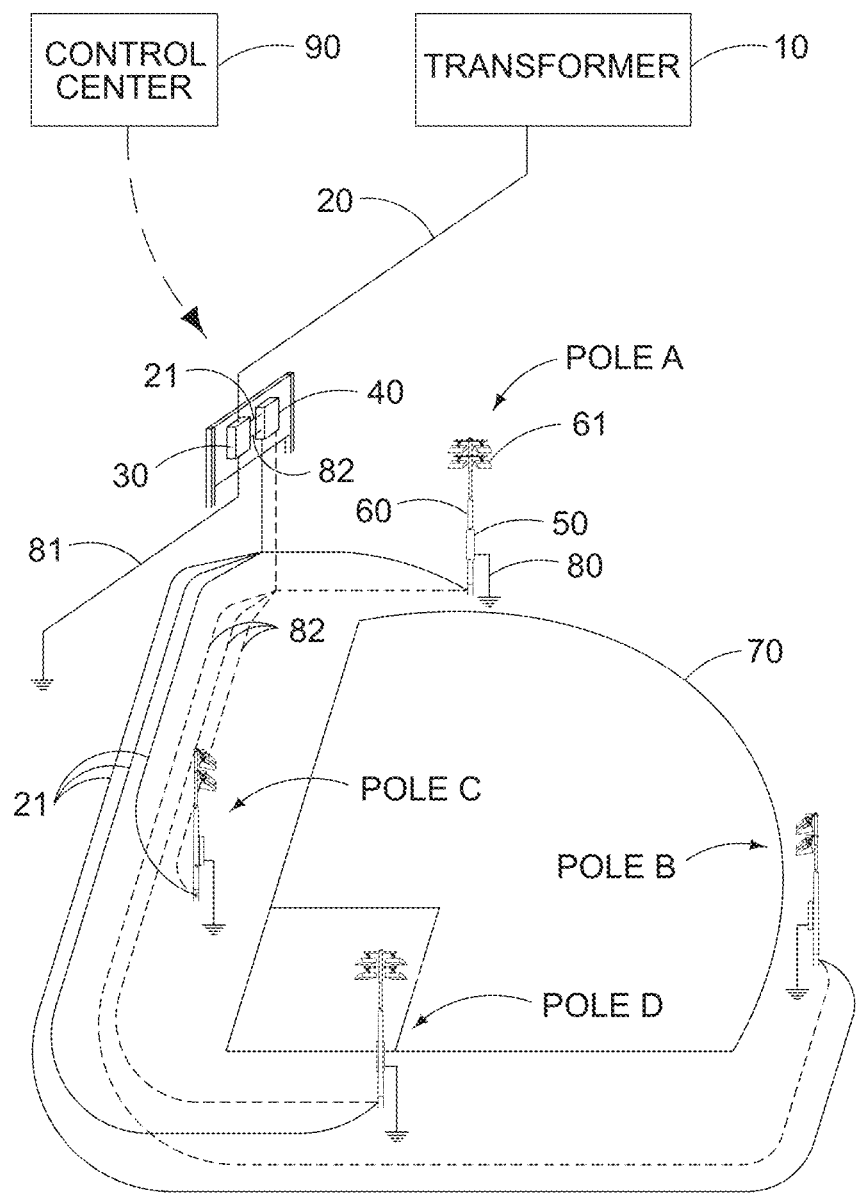
FIG. 1B illustrates a more complex lighting system according to existing art.
Figure 1C:
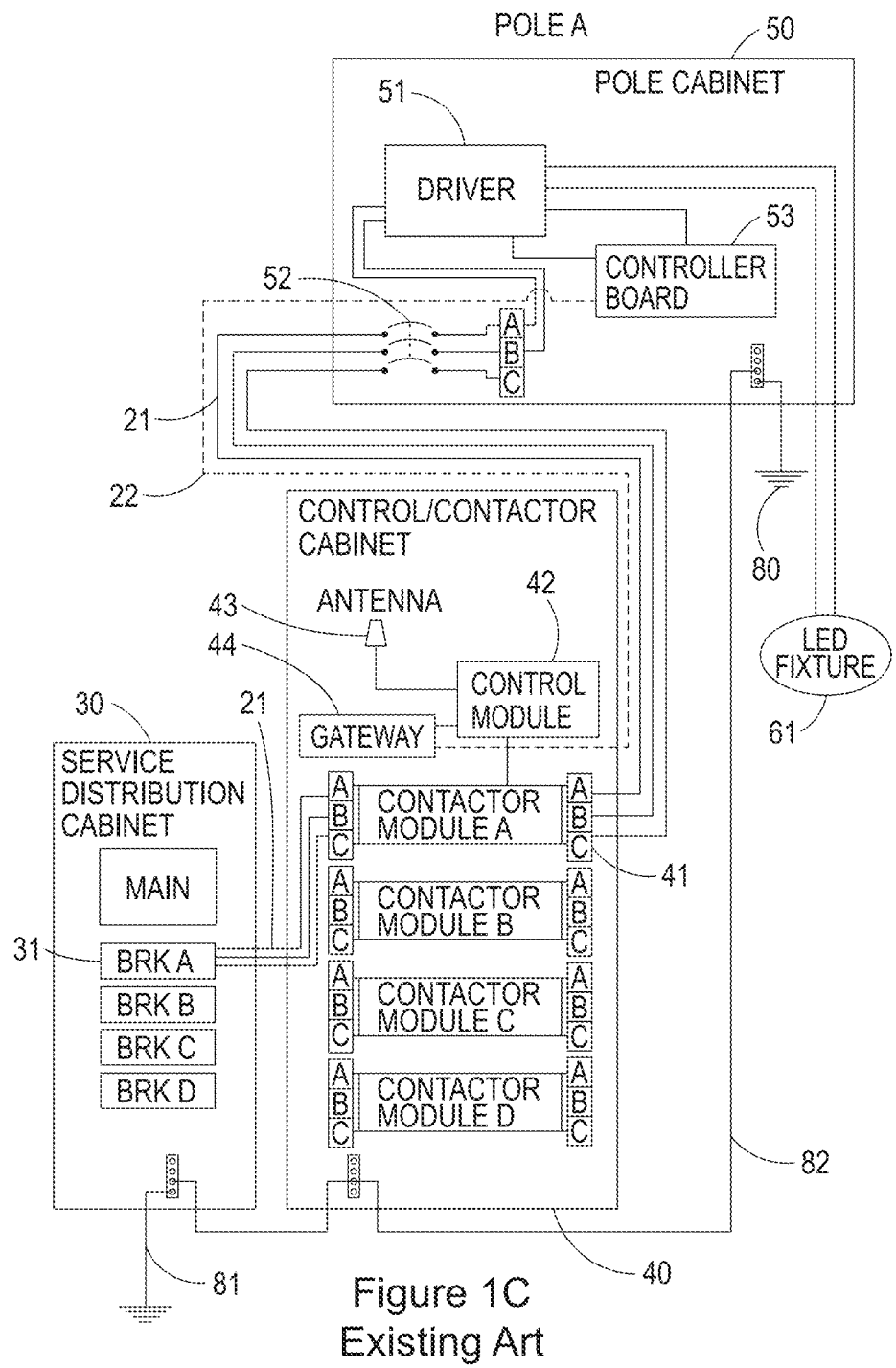
FIG. 1C illustrates a partial block diagram according to existing art corresponding to FIG. 1B.

The exemplary embodiment sets forth an LED lighting fixture employing a plurality of LEDs some subset of which have higher melanopic content than the others, operated according to a predetermined profile so as to provide both general lighting and circadian lighting without a perceivable shift in color or brightness. The aforementioned LED lighting fixture could take a number of forms—some of which are later described in greater detail—but generally speaking may be described according to FIGS. 1A-C. At its core, an LED lighting system generally comprises a power source 10 which distributes power via means 20 to a driver 51 which then distributes power which has been conditioned for use with LEDs via means 21/22 to one or more fixtures 61. The general principle illustrated in FIG. 1A is repeated and customized as needed for a specific task or general purpose, the corresponding lighting system becoming larger or more customized as needed; this is illustrated in FIGS. 1B and C for a baseball field. As can be seen from FIGS. 1B and C, a power source 10 generally comprises a transformer (e.g., from a utility company) which provides electrical power to a service distribution cabinet 30 via a distribution wire 20. Said electrical power travels from service distribution cabinet 30 to a control/contactor cabinet 40 via a power line 21 where it further travels to a pole cabinet 50 housed on each lighting support structure 60 (e.g. pole or other) via power line 21, and finally powers one or more LEDs; note that for clarity, only one complete circuit (from breaker 31 to contactor module 41 to LED fixture 61 at Pole A) is illustrated in FIG. 1C. The result is illumination of field 70. Of course, other considerations are important to note, even in a generic LED sports lighting system such as that illustrated in FIGS. 1B and C. For example, grounding to protect against adverse electrical effects (e.g., lightning) may be provided by earth grounds 80. Equipment grounding may likewise be provided via equipment grounds 8 in combination with ground wiring 82. Lastly, remote control capabilities may be enabled via a remote control center 90 which communicates wirelessly to a control module 42 via radio antenna 43 to provide dimming, on/off, or other scheduling information to driver 51 via a gateway 44 in communication with a controller board 53 connected by communication means 22—which could comprise hard wiring (e.g., RS-485, fiber), wireless communications (e.g., ZigBee), or could use existing wiring 22 in lieu of new wiring (e.g., powerline communications). Remote control functionality such as is described in U.S. Pat. No. 6,681,110, incorporated by reference herein in its entirety, and commercially available under the trade name CONTROL-LINK® from Musco Sports Lighting, LLC, Oskaloosa, Iowa, USA, may be useful in implementing predetermined operating profiles (e.g., power and/or duty cycle of each subset of LEDs) remotely—whether timed, periodic, or on command. Circuit breakers or fuses 52 could also be used to protect the circuitry.

A more specific exemplary embodiment, utilizing aspects of the generalized example described above, will now be described.

B. Exemplary Method and Apparatus Embodiment 1

As previously stated, according to aspects of the present invention a single light source (e.g. fixture, module, or other with a set of plurality of individual LED light sources) may be produced wherein both general purpose or background lighting and circadian lighting may be provided, and in a manner where perceivable brightness (e.g., as measured by a true brightness meter; see below) and perceivable color are both constant over the shift from an "awake" state to a "sleep" state. Said awake and sleep state generally correlate to a low melatonin production/metabolization rate and a high melatonin production/metabolization rate, respectively; alternatively, said awake and sleep state could be said to correlate to a more alert state and a more sedate state, respectively. It should be noted that it is not the primary purpose of the invention to determine if circadian lighting actually provides a biological/physiological benefit and if so, how to quantify or evaluate those benefits; rather the invention further enables the practice of what is becoming understood in the art to be beneficial aspects of providing circadian lighting.

To provide both general purpose lighting and circadian lighting from the same light source according to the present invention a light source (see, e.g., LED fixture 61, FIGS. 1A-C and 4A-5D) is envisioned to comprise at least two subsets of LEDs FIG. 4B; a first subset 62 having a high melanopic content and white in color, and a second subset 63 also white in color and having a low melanopic content. These two said subsets are constructed as metamers, i.e. they produce equal stimulation of the three cone retinal receptors. Said metamers are produced from combinations of specific LEDs following the method of Vienot, F et al., (2012) "Domain of metamers exciting intrinsically photosensitive retinal ganglion cells (ipRGCs) and rods", Journal of Optical Society of America A, February 2012, Vol. 29, No 2, pp. A366-A376, incorporated by reference in its entirety herein.

Based on present knowledge of the melanopsin efficiency function, calculations including most catalogued white light sources show that it is possible to achieve approximately a factor of five (5) between a high M/P source and a low M/P source. Note that this factor of 5 is a ratio and therefore is independent of choices of normalization of the melanopsin sensitivity function such as those introduced by Lucas et al (http://lucasgroup.lab.ls.manchester.ac.uk/research/measuringmelanopicilluluminance/website accessed 2016-05-25), incorporated by reference in its entirety herein. Further, said first and second subsets of LEDs must be of the same perceived color; namely, metamers of each other, i.e. they produce the same net outputs for the three retinal cones.

As such, according to a first step 1001 of a method 1000 (FIG. 2), a lighting designer or other person determines desired correlated color temperature (CCT) properties of the envisioned tunable, dual purpose LED circadian lighting system. Said lighting designer or other person may evaluate the general purpose of the lighting system (e.g., interior lighting, façade lighting, street lighting) or a task to be performed thereunder (e.g., high detail assembly work, general office work). This helps to inform what kind of white background light is to be employed, as well as where within the range of "white" the metameric pair of high M/P and low M/P sources should exist.

Table 1 below can be useful for this design process and illustrates CCT properties of several different well known light sources (and in addition some developed according to aspects of the present invention) with corresponding S/P and M/P values. M/P values shown are based on using unity normalization at the peak wavelength for the melanopsin sensitivity function. Values of M/P based on the CIE type normalization are obtained by applying to the M/P column in Table 1 the multiplicative factor 4.2146 based on the melanopic function provided by the reference above (Lucas et al).

TABLE 1

| Source | CCT | S/P | M/P |
|---|---|---|---|
| High Pressure Sodium | 1960 | 0.63 | 0.24 |
| High Pressure Mercury | 2970 | 0.81 | 0.29 |
| Warm White | 2850 | 1.03 | 0.43 |
| Warm White | 2900 | 1.09 | 0.47 |
| Metal Halide 27k | 2650 | 1.16 | 0.53 |
| Metal Halide 32k | 3320 | 1.36 | 0.63 |
| Metal Halide 30k | 2910 | 1.38 | 0.65 |
| Metal Halide 37k | 3440 | 1.48 | 0.70 |
| Metal Halide 40k | 3880 | 1.54 | 0.73 |
| Lite White | 4250 | 1.49 | 0.70 |
| RE Compact Fluorescent | 3170 | 1.19 | 0.48 |
| White Fluorescent | 3540 | 1.26 | 0.56 |
| Ultralume Fluorescent | 3130 | 1.28 | 0.55 |
| Cool White | 4060 | 1.30 | 0.57 |
| Cool White Deluxe | 4270 | 1.79 | 0.89 |
| LED Lamp | 5500 | 2.09 | 1.11 |
| Daylight Fluorescent | 5140 | 2.09 | 1.07 |
| Fluorescent 65k | 6380 | 2.26 | 1.18 |
| GE75 | 9530 | 2.62 | 1.43 |
| M/P LED | 17000 | 3.31 | 1.66 |
| M/P LED | 5700 | 2.51 | 1.18 |
| Musco (1) LED | 2400 | 2.6 | 1.43 |
| Musco (2) LED | 3100 | 1.2 | 0.52 |

If desired, additional color properties could be considered according to step 1001 of method 1000. For example, if an identified task requires accurate color rendering, a lighting designer or other person may opt to also define a relatively high (e.g., ≥60) color rendering index (CRI).

Figure 8B:
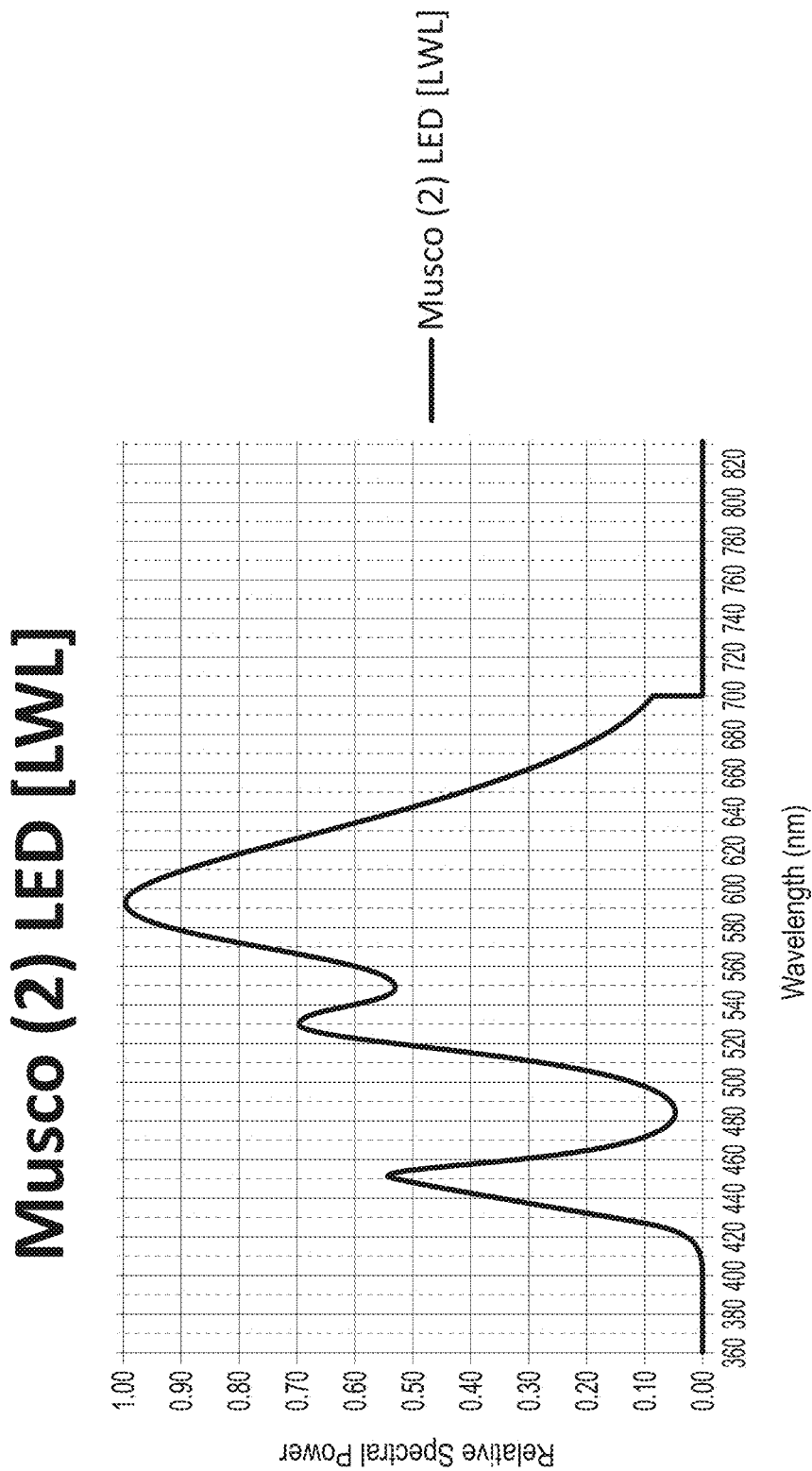

FIGS. 8A and 8B are graphs showing SPD for light sources Musco (1) and Musco (2), according to aspects of the invention and as referenced herein.

Figure 2:
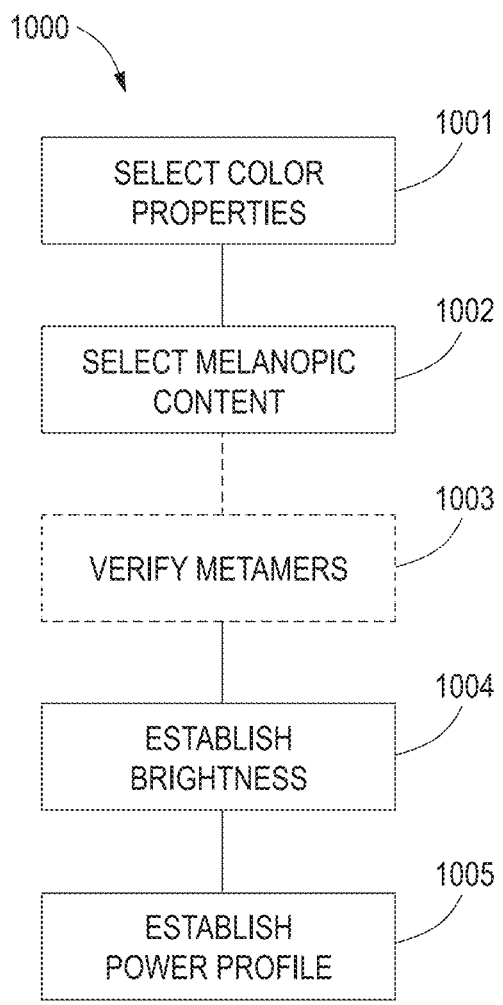
FIG. 2 illustrates in flowchart form one possible method of designing a lighting system capable of both general purpose and circadian lighting according to aspects of the present invention.

According to a second step 1002 of FIG. 2, the desired melanopic content range (i.e., the high melanopic content and the low melanopic content) are chosen. It is important to note that the melanopic content range can be chosen to be approximately within a single CCT if the ambient light is considered as important for task color fidelity. The choice of one melanopic content range over another may depend, at least in part, on manufacturability.

It should be noted that to fulfill the requirement of a melanopic efficient light source, LED designers would need to discontinue the practice of overlooking a key portion of the spectrum (around 488 nm), At one time, this portion of the spectrum was generally considered unimportant, since it was believed not to materially contribute to visual acuity, color rendering, etc.; now it is better understood to be a required factor to activate the melanopsin receptor. For example, FIG. 6A shows the "melanopic function" superimposed on the spectral function for a typical 5700K LED source. FIG. 6B shows values related to the curves of FIG. 6A. In this case, the peak of the melanopic curve is nearly perfectly aligned with a drop in the LED spectral curve such that this typical LED source can be seen to contain very low relative melanopic content, and therefore would not provide the benefits of high melanopic content light.

It is believed that the metamers ("Musco (1)" and "Musco (2)") reported on in the last two rows of Table 1 and used by Schlesselman et al can also be produced as a viable commercial light source using state-of-the-art practices related to LED phosphors. It should be noted that the invention as envisioned comprises at least a light source which has a relatively high percentage of energy in the band around 488 nm. In the case of the Musco (1) source, this is at about 0.40 relative energy with total energy normalized to 1.0 in the visible range. Thus, it may be seen that a high relative value for light at 488 nm, as well as light near the 488 nm value such as from 486 to 490 nm, 483 to 493 nm, or even from 478 to 498, or a still even broader range such as from 468 to 508 nm, especially when included specifically to increase melanopic content for a certain time period, while maintaining perceived brightness and color relative to a metameric light source having much lower melanopic content, is of high value in the industry. Specific examples of relative power envisioned include at least on the order of 0.20 between 478 to 498 nm, on the order of 0.30 between 483 to 493 nm, and on the order of 0.40 between 486 to 490 nm, as well as others that may be derived from the examples of SPD included herein or as may be appropriately developed.

Following step 1002, an optional step 1003 comprises verifying that the high melanopic content LED either by the manufacturer or independently through specialized field meters is actually a metamer of the low melanopic content LED and vice versa for the intended use; namely, that their SPDs are different but that they provide the same net cone stimulation and thus that the perceived ambient light will have same color. FIG. 3A shows a graphic screen capture from a calculational software application which might be used in optional step 1003. FIGS. 3B-E provide a set of renderings of the graphic of FIG. 3A illustrating areas 100, 110, 120, and 130 of the image of FIG. 3A in order to provide clear understanding of its content.

A fourth step 1004 comprises establishing a constant perceived brightness between the high melanopic content LED 1 and the low melanopic content LED as the overall melanopic output of the combined system varies according to a specific user schedule. As previously discussed, the recently discovered melanopsin receptor—more specifically, the intrinsically photosensitive retinal ganglion cells (ipRGCs)—has been observed to impact perceived brightness. Perceived brightness, as previously stated, is not the same as luminance or illuminance (despite language that may not state this clearly in some of the included references). Perceived brightness for a space is understood in accordance with Schlesselman et al., as the brightness sensation associated with the lighting of a large space (compared to centrally viewed objects) such as a room or an athletic field or even device background area. In general, such spatial brightness depends on both cone and melanopsin reception and has been determined by Schlesselman et al. as above to be described by augmenting the traditional output of the cones noted as P by the multiplicative factor $(M/P)z$ where the exponent z depends on the particular viewing conditions. For the conditions of a lighted sports field, Schlesselman et al above have empirically determined that the exponent has the value $0.32\pm0.02$ and has also been determined to be approximately the same for typical architectural environments. For other visual environments such as computer screens and mobile phones the exponent is also expected to be similar but could differ slightly. These concepts are shown explicitly by Equations 1 and 2 below that provide the auxiliary multiplicative factor that correlates with full or 'true' spatial brightness perception associated with the melanopic effect. The multiplicative factor as applied to the standard photopic illuminance quantity P for the general visual conditions described above is as follows.

General Case:

$$\text{Spatial Brightness } B=P(M/P)^z \qquad \text{Equation 1}$$

Special Cases as Described Above:

$$\text{Spatial Brightness } B=P(M/P)^{0.32} \qquad \text{Equation 2}$$

Thus, in general, if two sources with different M/P values (e.g. $LED_1$ and $LED_2$) are to produce the same spatial brightness then their respective photopic illuminances are adjusted following equation 1 as $$Lux_{LED1}/Lux_{LED2}=[M/P_{LED2}/M/P_{LED1}]^z \qquad \text{Equation 3}$$

which may be restated as:

$$Lux_{LED2}=Lux_{LED1}/[M/P_{LED2}/M/P_{LED1}]^z \qquad \text{Equation 3}$$

For the conditions of a lighted athletic field or for general architectural environments the general exponent 'z' is replaced by the numerical value 0.32 i.e. equation 3 becomes $$Lux_{LED1}/Lux_{LED2}=[M/P_{LED2}/M/P_{LED1}]^{0.32}$$

$$Lux_{LED2}=Lux_{LED1}/[M/P_{LED2}/M/P_{LED1}]^{0.32} \qquad \text{equation 4}$$

For the direct measurement of full spatial or 'true' brightness in the field, software is introduced into a traditional light meter to include incorporating the M/P values to adjust its output to provide a field measurement of 'true' brightness (thereby creating a spatial or "true" brightness meter). In particular, such a meter would use the dimensionally homogeneous M/P values based on the CIE type normalization where, in one example, the melanopsin sensitivity function has the value 683 at the wavelength of 555 nm. However, since the percentage difference of photopic lux between the two systems depends only on ratios of M/P values as per equations 3 and 4, that percentage is independent of the normalization method. It should be further noted that Schlesselman et al. as above have also shown that the exponents mentioned above are independent of normalization procedure.

As numerical examples of applying equation 4 and as an example of demonstrating the utility of the results of Schlesselman et al in terms of possible lighting energy savings, one may consider two cases of sources each generically for 'LED1' and 'LED2' based on the values provided in Table 1 with approximately equal CCT values, namely "cool white" with "cool white deluxe" and "Metal Halide 27K" with "Musco (1)". For each of these cases, assuming the lower M/P source provides 100 Lux of ambient illumination, the higher M/P sources achieve the same brightness perception with approximately 87 Lux or 73 Lux respectively. These latter values can be verified as producing equal brightness perception with the aforementioned spatial brightness meter. The particular numerical values are calculated using the second form of Equation 4 as follows:

For LED1=cool white and LED2=cool white deluxe $$Lux_{LED2}=Lux_{LED1}/[M/P_{LED2}/M/P_{LED1}]^{0.32}$$

$$Lux_{cool\ white\ deluxe}=Lux_{cool\ white}/[M/P_{cool\ white\ deluxe}/M/P_{cool\ white}]^{0.32}$$

$$Lux_{cool\ white\ deluxe}=100/[0.89/0.57]^{0.32}=86.7\ Lux$$

For LED1=Metal Halide 27k and LED2=Musco (1)

$$Lux_{LED2}=Lux_{LED1}/[M/P_{LED2}/M/P_{LED1}]^{0.32}$$

$$Lux_{Musco\ (1)}=Lux_{Metal\ Halide27k}/[M/P_{Musco(1)}/M/P_{Metal\ Halide27k}]^{0.32}$$

$$Lux_{Musco\ (1)}=100/[1.43/0.53]^{0.32}=72.8\ Lux$$

Knowing the photopic illuminance of both the high and low melanopic content sources (such as LEDs) to achieve the same perceived brightness, one may determine appropriate power inputs associated with said illuminances (i.e., the current needed to power the low and high melanopsin sources at their appropriate light levels). Determination of a power input to obtain a desired photometric output and measuring light using a light meter is well known in the art; of course, a traditional light meter could be used to verify that both the high and low melanopic content LEDs are operating at their desired photopic illuminance to achieve the desired energy savings.

For the invention proposed where the application is for dynamically controlling circadian stimulation, equation 3 serves as the indicator of the initial and final illuminance levels of the two metameric sources (high and low circadian stimulation) that assure equality in brightness perception. Dynamically and over the operating time period such stimulation moves from maximum stimulation (high M/P, e.g. LED1) to minimum stimulation (low M/P e.g. LED2). During the transition period, the illuminance values of both LED1 and LED2 are adjusted simultaneously to maintain constant brightness perception while constant color is assured during the transition as the two sources are metamers and thus any mixture of these metamers will retain the same color.

The algorithm for the illuminance profile for the two sources operating simultaneously in concert to achieve both constant color and brightness perception during the transition is set forth in equation 5 below.

$$(F_{LED1}+F_{LED2})^*[(F_{LED1}+cF_{LED2})/(F_{LED1}+F_{LED2})]^z=1 \qquad \text{Equation 5}$$

where: $F_{LED1}$=fractional photopic illuminance of the high melanopic content source calculated in Equation 1, and $0<F_{LED1}<1$ $F_{LED2}$=fractional photopic illuminance of the low melanopic content source calculated in Equation 1, and $0<F_{LED2}<c^{-z}$ $c=[M/P_{LED2}/M/P_{LED1}]$, and covering a wide range of possibilities, $\frac{1}{4}<c<4$ Equation 5 should be considered as a timed function—namely, that as power adjustments are made to LED1 to change its circadian efficiency, compensating power adjustments are made to LED2 to assure overall brightness perception associated with the total source pair remains constant. A user schedule may be applied such as changes every few minutes, in accordance with an existing building management system, or in accordance with local sunrise/sunset times, as a few non-limiting examples. Table 2 shows an example of such a power profile that could be used to vary melanopic content over time. As will be appreciated, other profiles based on other parameters are possible, according to need or desire.

For example, the operating profile of Table 2 (see also FIG. 9) could basically be the reverse. Instead of an 8 hour work shift starting at 8 PM, it could start at 8 AM. The % High M/P vs. % Low M/P would be reversed (e.g. at 8 AM 100% High M/P and 0% Low M/P). The profile would proceed to 9 AM and transition to 75% High M/P and 25% Low M/P, 11 AM 50% High M/P and 50% Low M/P, 1:00

PM 25% High M/P and 75% Low M/P; and 3:00 PM and 4:00 PM at 0% High M/P and 100% Low M/P.

TABLE 2

| Time (e.g. over an 8 hour work shift) | % High M/P | % Low M/P |
|---|---|---|
| 8:00 PM | 0 | 100 |
| 9:00 pm | 25 | 75 |
| 11:00 PM | 50 | 50 |
| 1:00 AM | 75 | 25 |
| 3:00 AM | 100 | 0 |
| 4:00 AM | 100 | 0 |

FIG. 9 shows a similar profile graphically representing a transition from low M/P light to high M/P light stepwise from 8 pm to 4 am changing from 100% low M/P light at 8 pm through 25%, 50%, 75%, and 100% high M/P light at 9 PM, 11 PM, 1 PM, 3 PM, and 4 PM respectively.

Equation 5 can also be specialized to the viewing conditions of a lighted athletic field or general architectural environments where the exponent takes on the value z=0.32 in which case equation 5 becomes equation 6 below:

$$(F_{LED1}+F_{LED2})*[(F_{LED1}+cF_{LED2})/(F_{LED1}+F_{LED2})]^{0.32}=1 \quad \text{Equation 6}$$

To illustrate the effects of using various values for e.g. FLED1+FLED2, FIG. 7 is a graph (using values 'f1', 'f2', and 'c' corresponding to FLED1, FLED2, and the exponent 0.32 respectively as used in Equations 4 and 6 showing the concomitant fractional change in f2 (=FLED2) to maintain equal brightness and color as f1 (=FLED1) changes from unity to zero per prescribed schedule for some listed values of the constant 'c' (Equation 5).

Thus, when the illuminance of the initial source (e.g. high circadian stimulation) is chosen based on particular design criteria, and once the power input to achieve said output is known, one utilizes the associated power control profile according to step 1005 of method 1000 to adjust the complimenting metameric source so that the net light from two sources in consort achieve constant perceived brightness while the circadian stimulation is varying. Said power profile could be readily implemented via software or communicated from an offsite position to a controller board for an associated subset of LEDs—for the scenario in FIGS. 1B and C from a remote control site 90 to antenna 43, to gateway 44, along communication means 22 to controller board 53, and finally to drivers 51. Said power profile could transition from the high melanopic content LEDs to the low melanopic content LEDs according to some regular period (e.g., a 1% power input change resulting in some fractional illuminance output change every several minutes), on demand (e.g., via manual power adjustment member such as a rheostat), or otherwise such as a preprogrammed schedule. So it can be seen that method 1000 sets forth a more comprehensive way of designing circadian lighting systems as compared to state-of-the-art practices insomuch that not only is color considered (i.e., the cone response), and not only are circadian rhythms considered (i.e., the biological/physiological response), and not only is brightness considered (i.e., the additionally controlled melanopic response), but all three are taken into account—and in a manner that maintains a perceivably constant color and spatial brightness perception. Method 1000 may be embodied in a variety of apparatuses so to produce a dual purpose LED lighting system (i.e., providing both general purpose lighting and circadian lighting); one such apparatus is illustrated in FIGS. 4A and B.

As can be seen from FIGS. 4A and B, LED fixture 61 generally comprises an array of LEDs; here 84 LEDs wired in two parallel strings (with 42 LEDs each wired in series) but physically spaced within the fixture such that the LEDs alternate from high melanopic content to low melanopic content. So looking at FIG. 4B, the first LED in the top row, upper left corner may be a high melanopic content LED, the next one to it may be a low melanopic content LED, the next one a high melanopic content LED, and so on. Alternating physical placement of the two subset of LEDs in this manner ensures the beam pattern and light uniformity (which is critical for general purpose and tasks performed thereunder) is maintained as the high melanopic content LEDs which are at full output in the morning are transitioned to low or no output in the evening (and vice versa for the low melanopic content LEDs). It should be noted that control of two separate strings would require either two drivers or a single driver with two outputs, but these are readily commercially available and in many cases are still a lower cost option to a user than having to purchase a general purpose lighting system and a circadian lighting system.

Figure 5A:
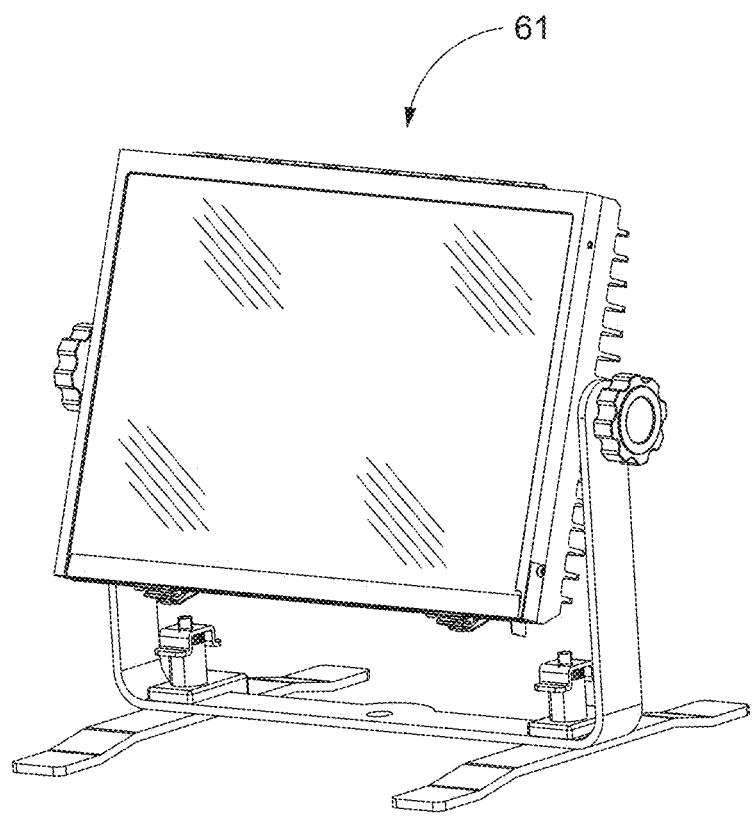
Figure 5B:
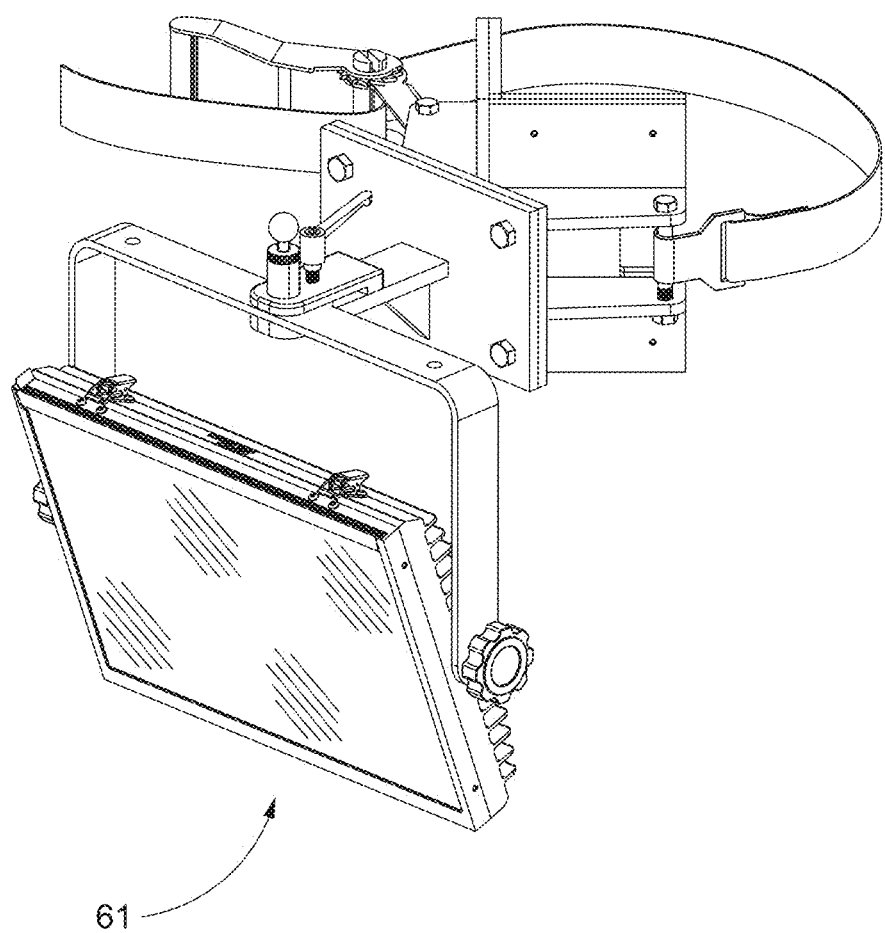
Figure 5C:
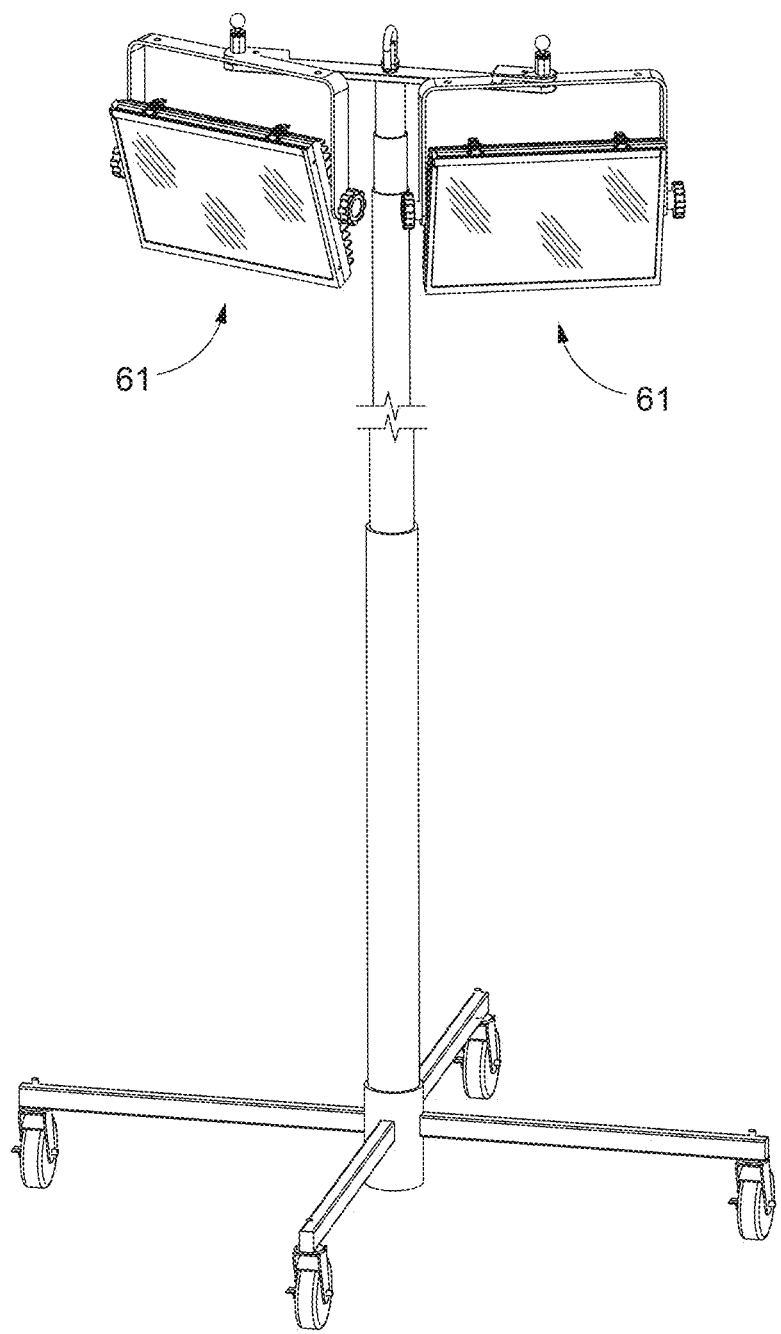

LED fixture 61 further comprises a fixture housing 11 constructed of aluminum (or other thermally conductive alloy) with integral finned heat sink 6, which together with transparent lens 5, encloses the LED light sources and optics panel 7 with interchangeable optics 8 at points 1. LED fixture 61 could be used with a variety of support structures so to enable operation in a variety of environments or for a variety of tasks. In addition to a sports lighting application such as that illustrated in FIGS. 1B and C, LED fixtures could be ground mounted for architectural lighting (FIG. 5A), affixed to a strapping device which could be further affixed to an existing feature (e.g., tree) for temporary or event lighting (FIG. 5B), mounted to an adjustable jig for mobilized, targeted lighting (FIG. 5C), or recessed for general purpose interior lighting (FIG. 5D). Of course, other applications are possible, and envisioned—and any of the aforementioned applications may have different requirements to fully realize the desired biological/physiological benefits of circadian lighting. For example, while the arrangement of FIG. 5A could be used to illuminate outdoor sculptures (e.g., at an outdoor art event) and where the low melanopic content lights are gradually becoming more dominant near closing time (e.g., to provide a non-visual cue to patrons to leave and "wind down" for the evening), the opposite may be appropriate for a night worker at a port using the arrangement of FIG. 5C. It may be preferable to start with the low melanopic content LEDs fully powered and increase the dominance of the high melanopic content LEDs over the course of a night shift (e.g., to encourage alertness). Either of these scenarios may benefit from aspects according to the present invention.

The invention may take many forms and embodiments. The aforementioned examples are but a few of those. To give some sense of some options and alternatives, a few examples are given below.

C. Options and Alternatives

The present invention sets forth methods, apparatus, and systems for providing both general purpose lighting and circadian active lighting from the same lighting system. It is important to note that this does not place a limitation on the use of aspects according to the present invention. A person could operate a lighting system according to aspects of the present invention (e.g. a lighting system having both high melanopic content sources and low melanopic content sources or even a single source whose spectral output can be dynamically adjusted) so as to output any desired melanopic content within the range of the included sources; this could range from utilizing from 0 to 100%, or anywhere in between, of the high melanopic content sources and from 0 to 100%, or anywhere in between, of the low melanopic content sources according to a schedule that could include any interval of timing of any of the melanopic content selections even up to 100% duty cycle at any of the extremes (i.e. ranging from operating full time at 100% high melanopic content to 100% low melanopic content sources or any set point in between these extremes) and not deviate from aspects of the present invention.

With regards to the various formulas set forth, it should be noted that these could differ and not depart from at least some aspects according to the present invention. For example, since melanopsin/melanopic content is a relatively new concept in the field of vision science, it may be preferable to use a different ratio to represent the non-visual response to perceived brightness (even if not a perfect substitution under all testing conditions). It has been found (see Schlesselman et al) that melanopic content is highly correlateable to the ratio of scotopic to photopic outputs (S/P) rather similarly to M/P—where S represents the convolution of the source SPD with the scotopic luminous efficiency function (V'(λ)) as sourced from the Commission internationale de l'éclairage (CIE). The high correlation between S/P and M/P allows the data to be analyzed with S/P as the functional spectral factor just as well as M/P. In such an instance, Equation 3 would be modified to become Equation 7 and Equation 6 would be modified to become Equation 8.

$$\text{Lux}_{LED1}/\text{Lux}_{LED2} = [S/P_{LED2}/P_{LED1}]^{0.436} \quad \text{Equation 7}$$

where: Lux is measured photopic luminance $$(F_{LED1}+F_{LED2})*[(F_{LED1}+dF_{LED2})/(F_{LED1}+F_{LED2})]^{0.436}=1 \quad \text{Equation 8}$$

where: $F_{LED1}$=fractional photopic illuminance of the high melanopic content source calculated in Equation 1, and $0<F_{LED1}<1$ $F_{LED2}$=fractional photopic illuminance of the low melanopic content source calculated in Equation 1, and $0<F_{LED2}<c^{-0.436}$ $d=[(S/P_{LED2})/(S/P_{LED1})]$, and $1/5<c<5$ As another example, instead of timed power adjustments (e.g., where input current is increased or reduced), timed duty cycles of prescribed sources may be adjusted to facilitate a transition from a high melanopic content source to a low melanopic content source and vice versa.

D. IES #1 (Supplemental Information)

Brightness judgments in a simulated sports field correlate with the S/P value of light sources.

Bradley Schlesselman, Myron Gordin, Larry Boxler[1], Jason Schutz, Sam Berman[2], Brian Liebel[2] and Robert Clear[2]

Musco Sports Lighting, LLC, 100 1$^{st}$ Avenue West, Oskaloosa, Iowa 52577

Abstract:

Brightness perception in a simulated sports field was evaluated for photopically equal and constant color lighting but of different spectral content (metamers). A simulated sports field of dimensions 20×30 feet was constructed in an enclosed space and lit to the distribution of photometric conditions (both light and dark) approximating those measured at night in an operating full size illuminated sports field. Fifty-seven subjects comprising 3 age groups (18-30 years, 31-50 yrs and >50 years) were selected and sat in a chair positioned at an edge and midpoint of the simulated field, providing a binocular and unobstructed view of both the lit "field" and dark surround. The illuminance levels were 60,150, and 400 vertical lux at eye level in the direction of gaze, corresponding to those measured for spectators and performers in an operating field. Subjects were Musco employees or their family that had no special knowledge in lighting and were unaware of the study purpose. The study utilized theatrical luminaires with multiple and different colored LED sources which could be combined to form four pairs of whitish metamers, each pair consisting of one metamer having a relatively higher S/P ratio compared to the other. Two pairs had relatively higher nominal CCT values than the other two pairs, and within each CCT set of metamers, one pair had a wide spread between the high and low S/P ratio metamer, while the other pair had a relatively smaller difference between the S/P ratios. The S/P values ranged approximately from 1.2 to 4 and the difference between the S/P values for a compared pair varied between 0.72 and 1.86. The conventional CCT values ranged from nominal 2700K to 6700K.

Subjects compared the perceived brightness of the illuminated field under each metameric pair where the illuminance measured at the eye was equal for each of the two sources within the compared pair. The comparison was judged while subjects viewed repeated switching between the paired lightings. Subjects were asked to focus on an iPad mini with a video image of a lava lamp placed in the middle of the simulated field, and judge which of the 2 lighting conditions appeared brighter. 47 Subjects completed this test that included all four metameric pairs at both 60 and 150 lux, and one pair at 400 lux, for a total of 423 total spectral comparisons. The result obtained was that 375 out of those 423 comparisons had the higher S/P value light sources chosen as the lighting that gave the illuminated field a brighter appearance. This result yields an unbiased estimate of 88.5%±1.6% in favor of the higher S/P as perceived brighter with a miniscule p-value or probability of chance occurrence of approximately $10^{-134}$. The results were highly significant for all age groups.

To establish a possible objective correlate associated with the brightness perceptions, pupil size was measured employing infrared pupilometry for two of the metameric pairs at the 150 vertical Lux light level for 40 subjects. Results showed that on average pupil sizes were significantly smaller for the higher S/P spectra under otherwise identical lighting conditions, and were also in quantitative agreement with past observations although not necessarily the causal factor in brightness perception.

Background:

Previous studies Berman et al (1990), Brown et al (2012), Royer &Houser (2012) have shown that in conditions of full field of view lightings of the same color but of different spectral content and also with equal photopic luminance (metamers) are not perceived as equally bright. Current understanding of these observations [Brown et al (2012), Ecker et al, (2010)] is that they are likely a result of the responses of the non-image forming melanopsin photoreceptor widely distributed in the retina of the eye and whose spectral responses are not included in the determination of photopic luminance. Earlier work by Berman et al (1990) and prior to the discovery of the melanopsin receptor correlated full field brightness perception with the spectral content of metamers by employing an empirically determined correlation based on the S/P value of the metamer spectral content. Later calculations showed that for polychromatic light sources typical of lighting practice that there was a very high correlation (over 99%) between the S/P values and the melanopic content of these sources [Berman (2008), Berman &Clear (2008,2014)]. Although recent research [Royer &Houser (2012)] determined that photopic luminance did not predict equal brightness perception for their metamers, it was also concluded that the use of S/P failed as the spectral factor for correlating their results leaving uncertainty as to both the mechanisms behind the brightness perceptions and a practical guidance for lighting practice.

Study Objectives:

Over the past several years Musco engineers noticed that their brightness perceptions of lit athletic fields appeared to depend on the spectral content of the lighting. Such perceptions could possibly be due to vision related color effects resulting from differences in source colors (Harrington 1954), or effects of differences in source melanopic content (Bailes 2010) or perhaps a concurrence of both effects. In view of the past research efforts described above it was the intent of Musco to conduct a study where the 2 visual percepts were separated and to first examine the non-color effects. Thus, the objectives of this investigation were to provide a more rational explanation of the field observations in terms of the most current lighting and vision science.

Methods:

Description of Test Room:

In order to accomplish these objectives a test room was designed to provide a reasonable simulation of an existing athletic field. A recreational soccer field of dimensions 240 feet by 150 feet lit to conventional light levels was chosen as a typical real field from which to design the simulation. Measurements of vertical illuminance at the eye were taken at this representative field from the perspective of a player in the field and a spectator on the side, yielding nominal values of about 150 and 60 vertical Lux respectively corresponding to a range of 250 to 300 Lux of horizontal illuminance. The visual lighting perspective gained by a person standing on one side of the field and at the midpoint would provide a view with approximately ¾ of the total visual solid angle as essentially dark and the remaining lit by the field luminaires.

Figure 10A:
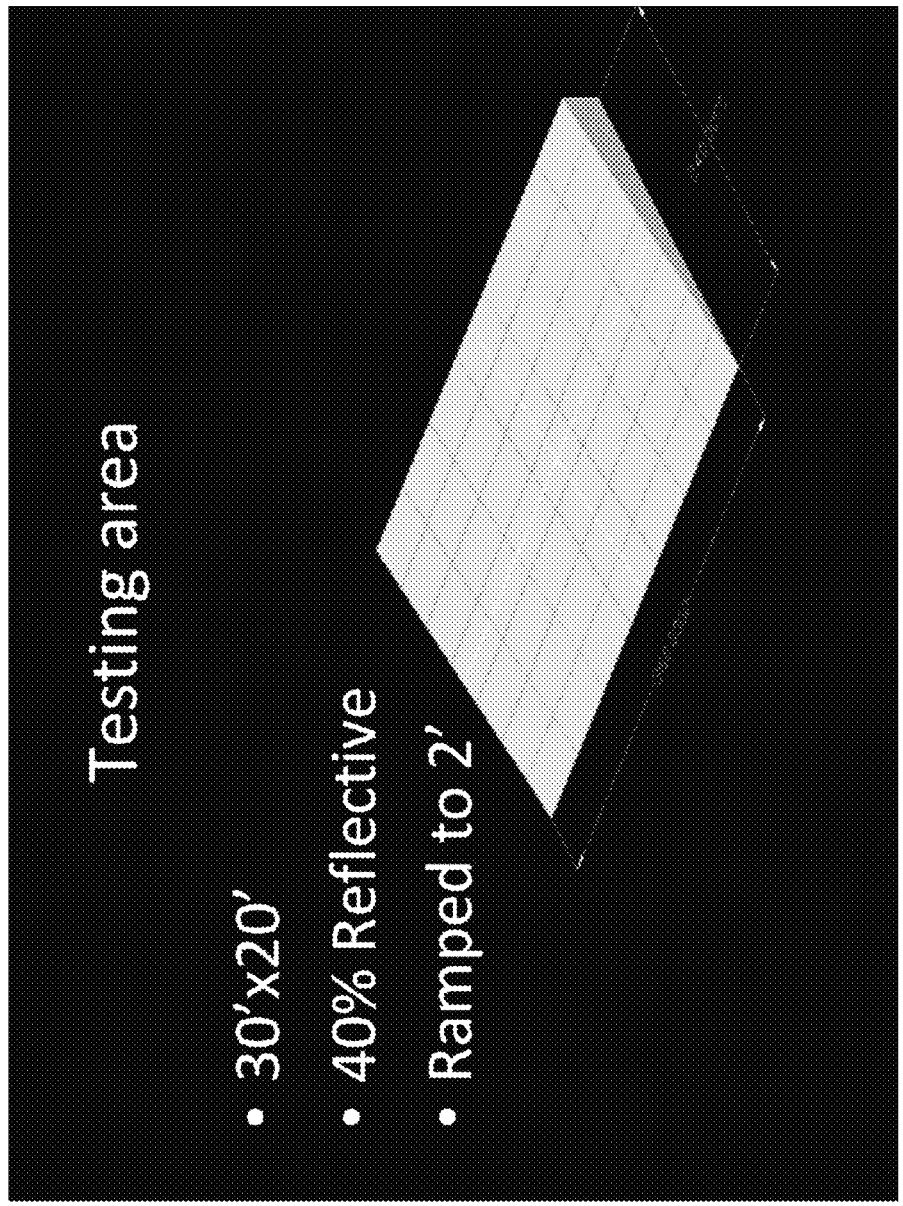
Figure 10B:
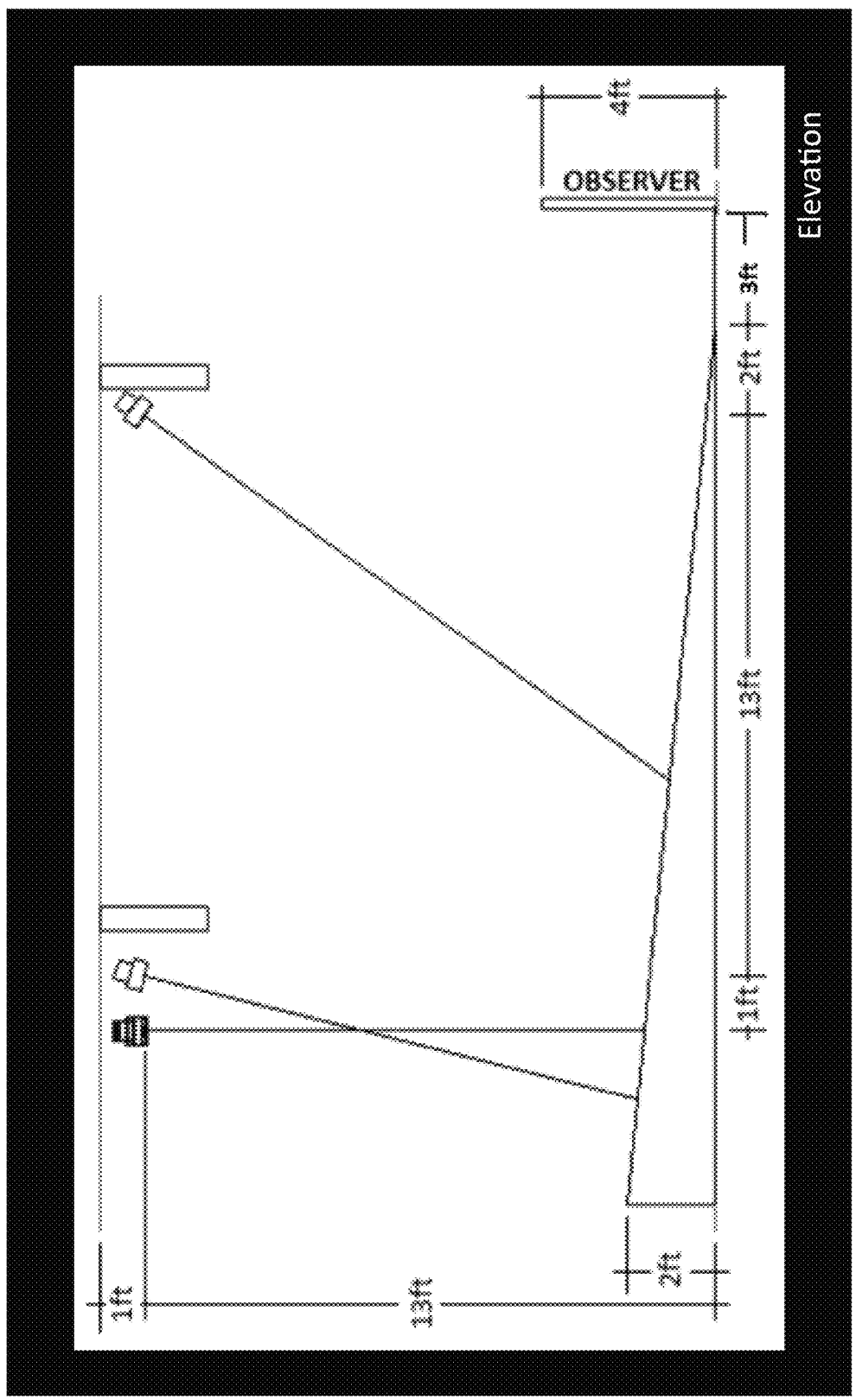
Figure 10C:
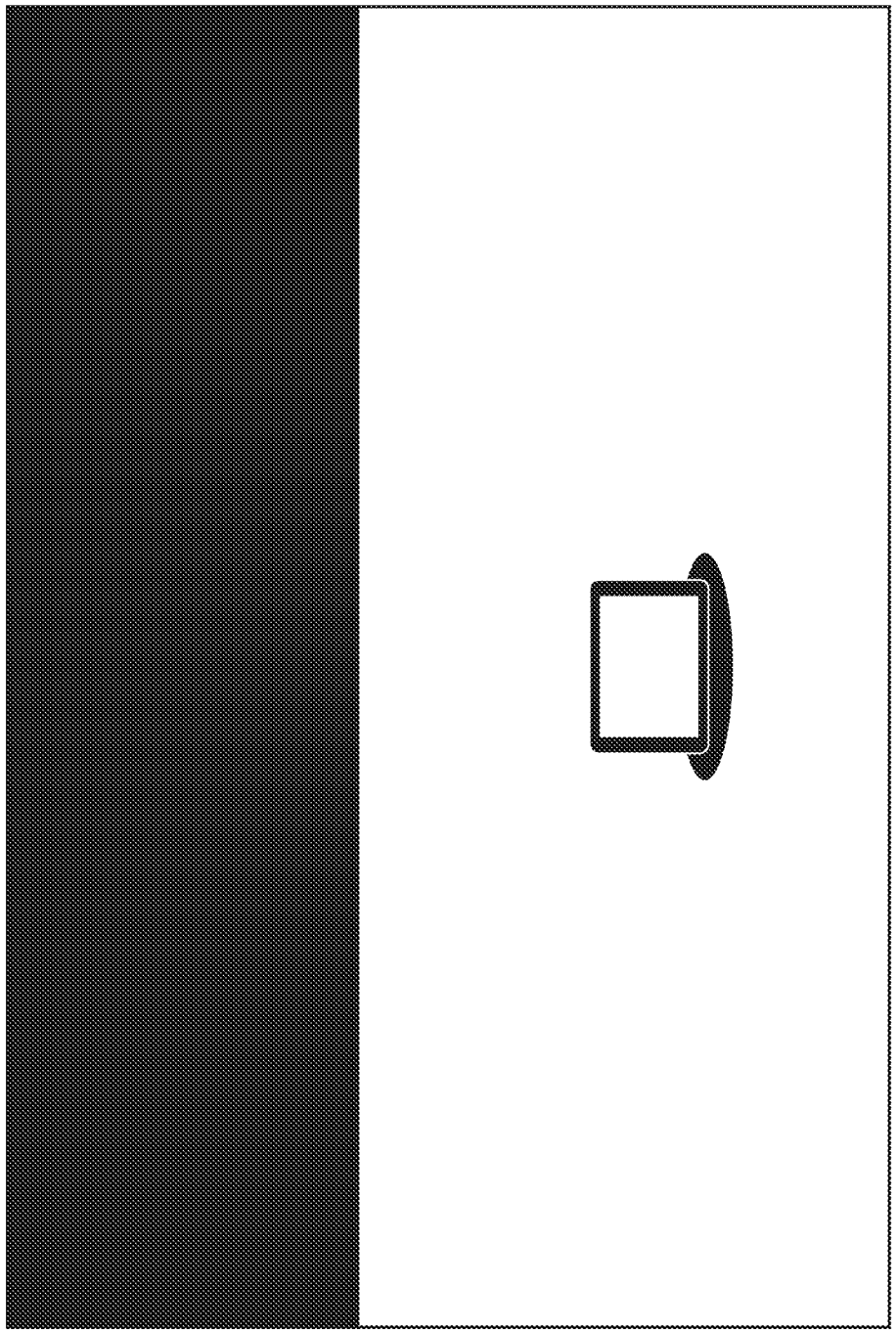
Figure 10D:
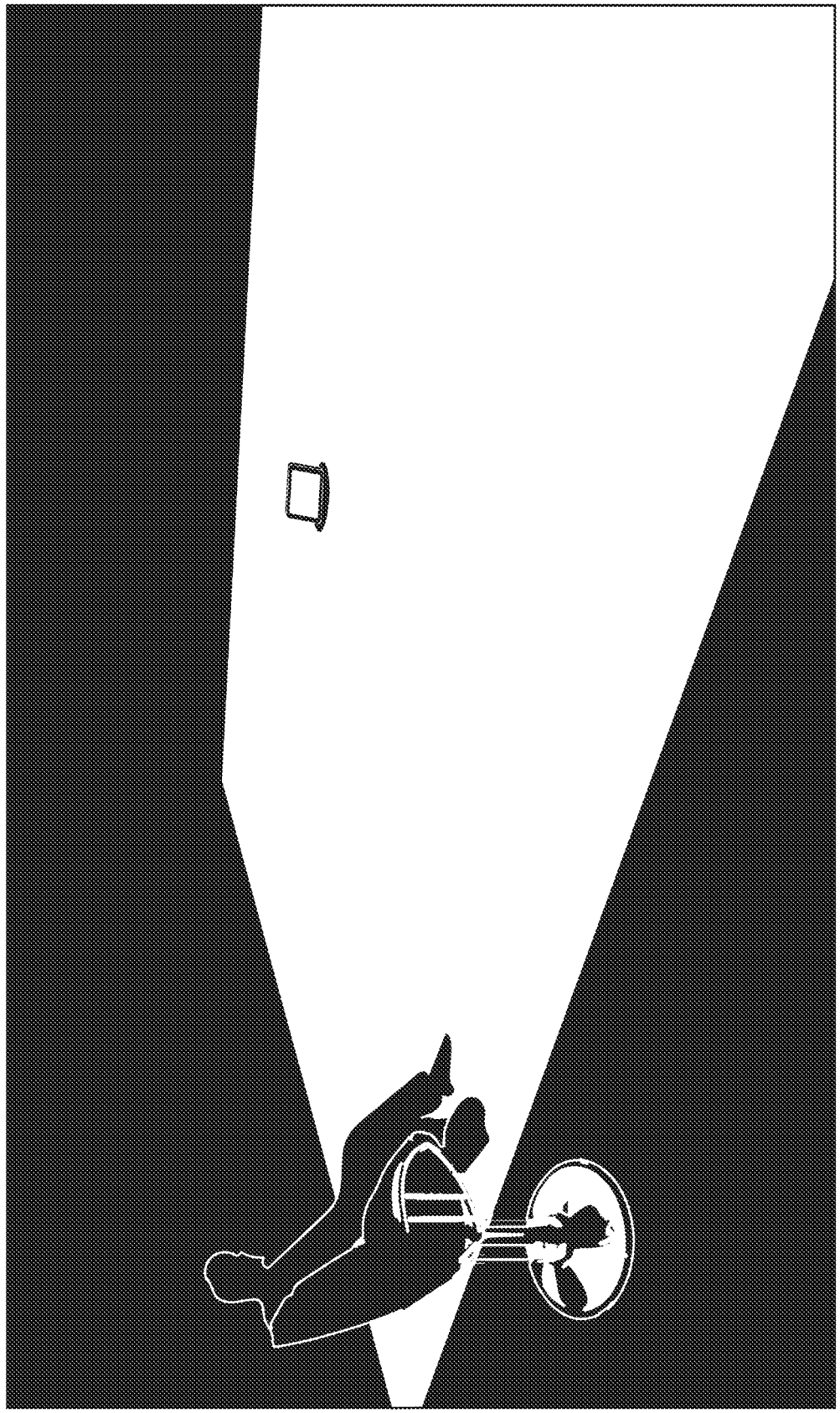

A 30' wide by 20' deep simulated test field was constructed inside a large hall, lit so that about ¾ of the visual solid angle was in the dark from the perspective of the subject situated at the midpoint of the longer dimension and at the front end of the shorter dimension. The design of the simulated field was based on actual field condition sight lines. FIGS. 10A, 10B and 10C show a perspective view of the simulated field construction, a cross-sectional drawing, and a photograph, respectively, of the test environment. The simulation of the field was accomplished by lighting only the lit portion of the test floor, which was painted a spectrally neutral, matte gray color and had an incline of 7.5 degrees to establish concordance in the end point viewing angle of the subject as would occur on the real field. The dark portion was obtained by using matt black fabric that was placed to surround the lit portion of the test space.

Achieving the necessary illuminance to simulate the field conditions required both direct lighting on the test field floor plane to yield a field luminance distribution approximating that of the real sports field, along with the addition of several overhead fixtures that provided the majority of vertical illuminance at the observer eye that would come from typical high mast sports lighting luminaires in real conditions. Attention was paid to assure that these overhead fixtures were not directly visible by the subject as well as to minimizing possible direct glare due to the proximity of these overhead fixtures in relation to the subject position (see FIGS. 10A-E).

For the study, subjects sat in a chair at the midpoint of the long dimension at the edge of the lit floor as seen in FIG. 10C and viewed an iPad Mini tablet placed in line with center of the long dimension and at the middle of the lit floor. The iPad screen subtended essentially a foveal visual angle of about 3 degrees from the subject position and provided a fixation point. The iPad was set to display slow temporal screen variations by showing a simulated lava lamp scene of fixed color thereby helping to reduce boredom and to assure that the direction of gaze would be similar for all subjects. The iPad was placed in the center of a 12 inch diameter black circle (FIGS. 10C and 10D) and together these essentially foveal objects help to minimize the transient 'Maxwell Spots' that can be sensed in the central visual field when switching between test metamers and when the lit field of view extends much beyond the fovea.

Lighting System:

The lighting for the test facility was provided by theatrical fixtures suitably placed so that the lighting distribution on the floor was uniform (10 fixtures), with an additional 5 fixtures adjusted to achieve the illuminance at the eye in the direction of gaze (DOG illuminance), namely the test values of 60 and 150 Lux. At maximum output it was also possible to achieve a higher value of approximately 400 DOG Lux and some testing was undertaken at that higher level.

Figure 10E:
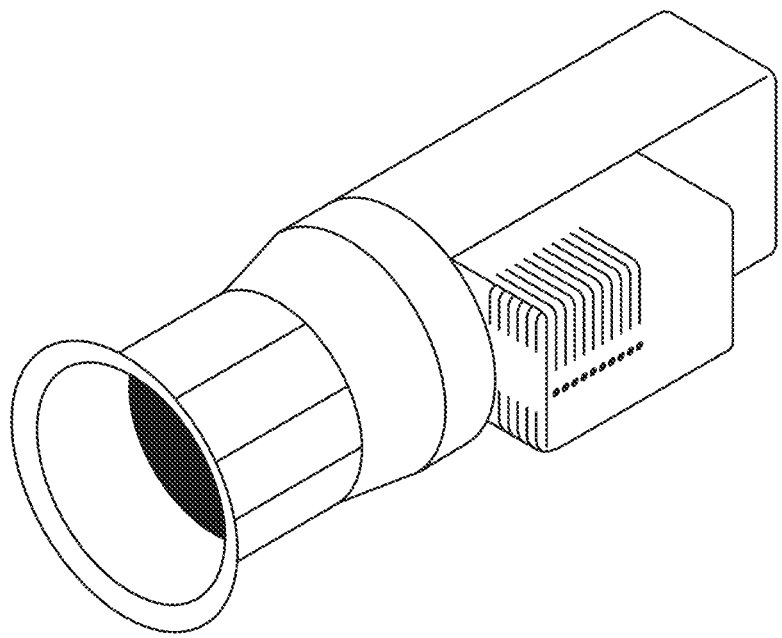

The fixtures were ETC Source Four LED theatrical luminaires with an array of 60 Luxeon Rebel emitters that consisted of 7 spectrally different colored LEDs (See FIG. 10E for a photo). The specific spectral power distributions (SPDs) were chosen so that several overall whitish metamers could be obtained but with different S/P content and CCT values (see section below on metamer design). A programmable DMX controller was used to yield the particular light levels and metamer combinations, where the LED light level output had a linear relationship with DMX value. The DMX controller allowed for rapid switching between metamers that would eventually be compared for brightness perception with a total transition time interval of 1 second. In addition, the controller allowed metamerism to be maintained during the switching with a gradual shift in S/P values to its end point value by transitioning over 5 intermediate metameric stages each of 200-millisecond interval thereby minimizing transient perceptual effects.

Metamer Design:

The goal was to create whitish metamers of different melanopic spectral content or analogously different S/P spectral content as employed in the earlier studies by Berman et al (1990) and Brown et al (2012). Since color differences will contribute to brightness perception even at equal photopic luminance, the revealing of possible non-cone mechanisms requires that the viewed scenes of different spectral content have identical cone stimulation and therefore perceived color but have different melanopic or equivalently S/P content.

Typically source metamerism is determined by employing the conventional CIE color space such as the CIE 1931 2° or CIE 1964 10° observer color space and this was indicated as the procedure used by Royer &Houser (2012). There are however, deficiencies in the conventional CIE color matching functions when applied to forming perceived metamers that have been previously noted in the literature (Boynton 1996, Shaw 1999). In particular, Stockman & Sharpe (1996, 1999,2000) have presented an alternative color space that addresses those deficiencies. The cone fundamentals of the alternative color space are detailed in CIE (2006) "Fundamental chromaticity diagram with physiological axes—Part 1 Technical Report 170-1". For the purposes of this study metamerism is obtained by equal stimulation of those cone functions for the metamers and was determined for the 7 LED sources by employing the methodology described by Vienot et al (2012) as based on Cohen & Kappauf (1982, 1985). These constructions provide much superior perceived metamers when compared to constructions based on the CIE protocol of equal chromaticities.

Figure 10F:
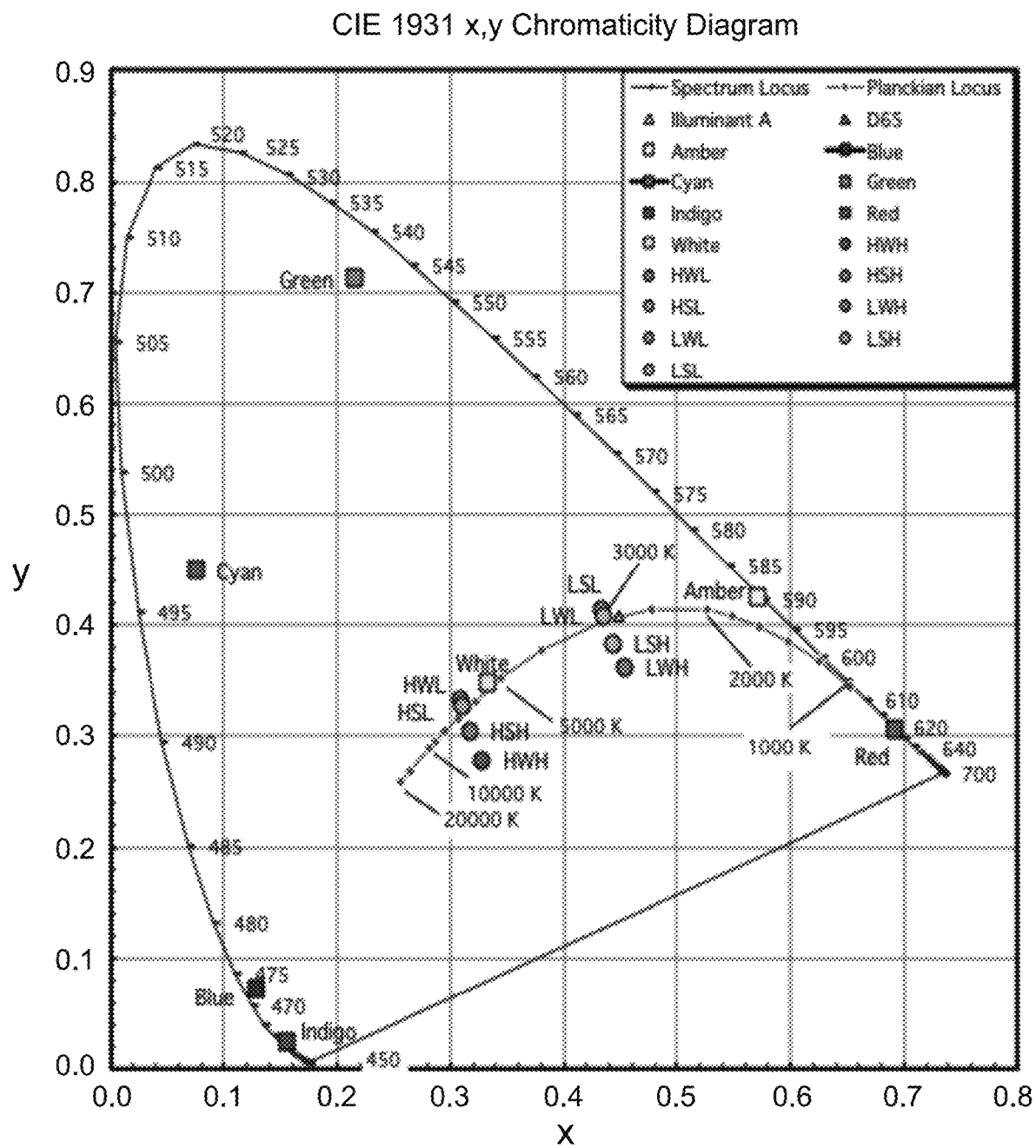

Note that the CCT values associated with the metamers and indicated in this study are calculated by employing the conventional CIE chromaticity system as applied to the SPD's of the test metamers and are referred to here as conventional or traditional CCT values. Since these test metamers do not have precisely equal CIE chromaticity values our calculated CIE CCT's will also be different for a compared metamer, but even so observers do not perceive color differences as metamers based on the Stockman/Sharpe functions are perceived as more identical. On the other hand, should alternate CCT values based on a color space employing the Stockman/Sharpe cone fundamentals be evaluated then those alternate CCT values would be identical for metamers constructed from those fundamentals. FIG. 10F shows the location of our metamers on a conventional chromaticity diagram where the slight shifts from chromaticity equality are indicated.

Figure 10G:
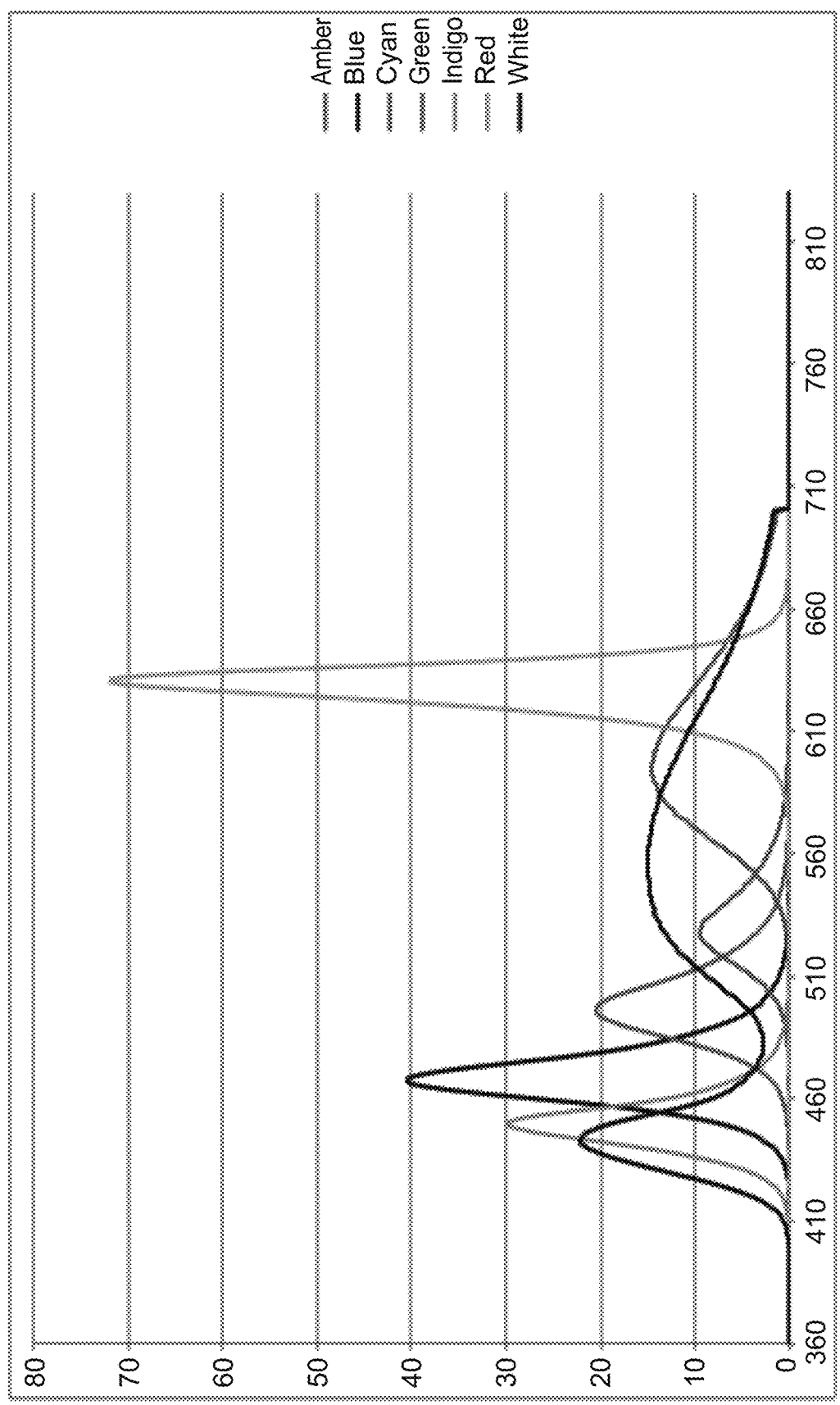
Figure 10H:
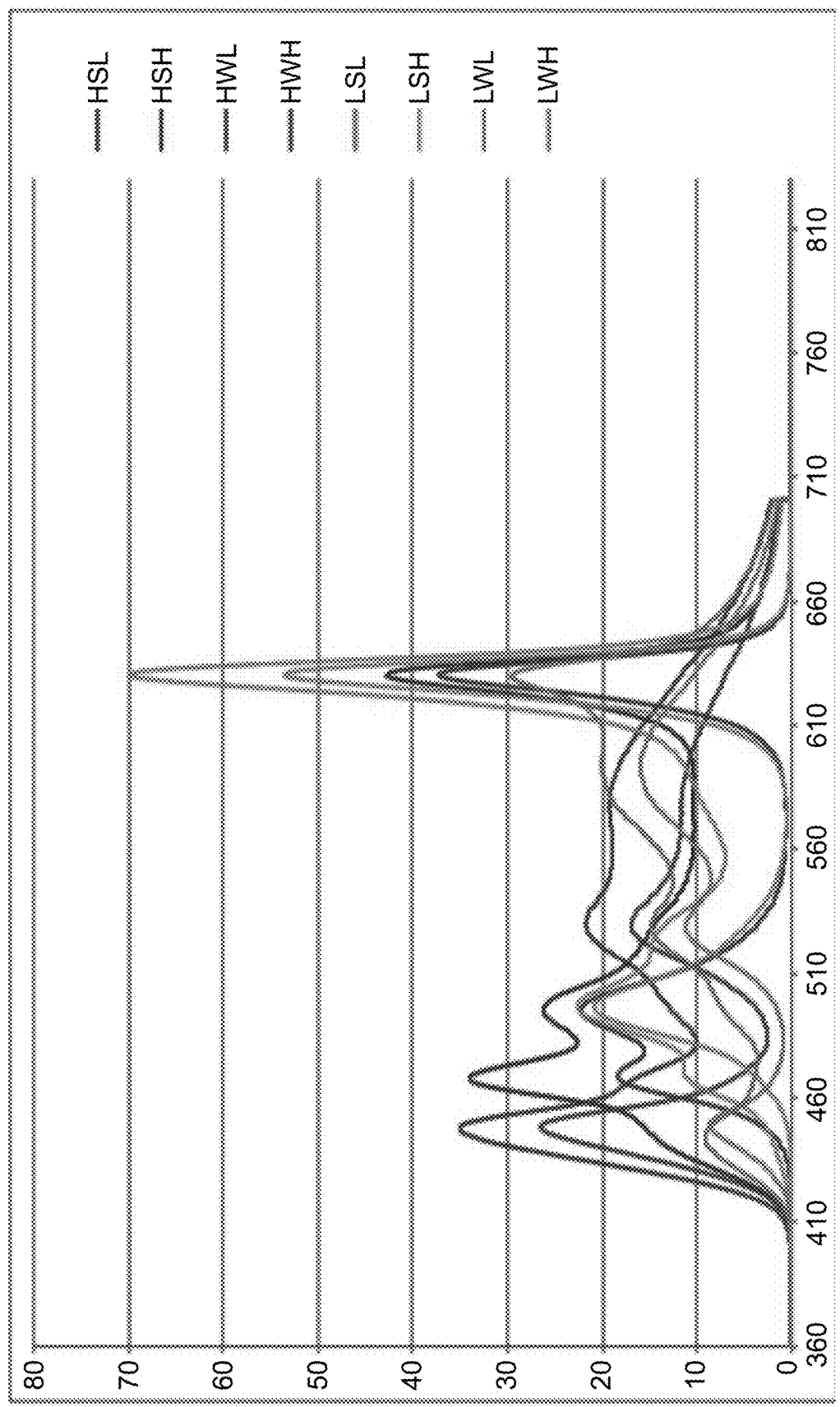

Four metameric pairs were constructed using the combination of LEDs within the ETC fixtures. The pairs were designed such that two pairs had a relatively higher conventional CCT than the other two pairs, and within each of the two pairs with differing conventional CCTs there was one pair with a wide spread between S/P values and one pair with a smaller spread between S/P values. The resulting metamers are described below in the following tables and figures:

- Table 1 indicates the CIE x,y chromaticity coordinates of the (7) LED's and the resultant (8) metamers
- FIG. 10F shows the locations of Table 1 values on a conventional CIE chromaticity diagram
- FIG. 10G shows a graph of the SPD's of the (7) LEDs that compose the metamers and listed in Table 1
- FIG. 10H shows a spectral graph of the (8) metamers listed in Table 1

TABLE 1

CIE x, y Coordinates of the seven LED sources and the resultant metamers.

CIE CHROMATICITY COORDINATES

| ETC LED Sources | | | X | Y |
|---|---|---|---|---|
| Amber | | | 0.5700883 | 0.4254393 |
| Blue | | | 0.1283426 | 0.0719665 |
| Cyan | | | 0.0747183 | 0.4494363 |
| Green | | | 0.2152694 | 0.7123734 |
| Indigo | | | 0.1549665 | 0.0244588 |
| Red | | | 0.6914472 | 0.3060068 |
| White | | | 0.3321667 | 0.3485219 |

| Metamer Pairs | | S/P | Code | X | Y |
|---|---|---|---|---|---|
| Pair 1 | High CCT | Hi | HWH | 0.3277019 | 0.2778902 |
| | Wide S/P Spread | Lo | HWL | 0.3086062 | 0.3341716 |
| Pair 2 | High CCT | Hi | HSH | 0.3167614 | 0.3053155 |
| | Small S/P Spread | Lo | HSL | 0.3097961 | 0.3278254 |

TABLE 1-continued

CIE x, y Coordinates of the seven LED sources and the resultant metamers.

CIE CHROMATICITY COORDINATES

| Pair 3 | Low CCT | Hi | LWH | 0.4534897 | 0.3622677 |
|---|---|---|---|---|---|
| | Wide S/P Spread | Lo | LWL | 0.4322281 | 0.4145167 |
| Pair 4 | Low CCT | Hi | LSH | 0.4430859 | 0.3839001 |
| | Small S/P Spread | Lo | LSL | 0.4348558 | 0.4085055 |

Lighting Conditions:

Each metameric pair was established, including the incremental steps, using the method described above. Once the fixtures were put in place to achieve the uniformity and Direction of Gaze (DOG) illuminance targets to simulate the sports field conditions, light measurements were taken to record the SPD and resultant S/P ratio and CCT of each metamer. Table 2 summarizes the measured values of the metamers:

TABLE 2

Lighting Conditions: Vertical DOG Illuminance, S/P values and CCT values

| | | | Illuminance Levels | | | Illuminance Levels | | |
|---|---|---|---|---|---|---|---|---|
| Pair | Description | Code | 60 S/P | 150 S/P | 400 S/P | 60 CCT | 150 CCT | 400 CCT |
| 1 | High CCT | HWH | 3.952 | 3.898 | | 5653 | 5475 | |
| | Wide S/P Spread | HWL | 2.088 | 2.064 | | 6580 | 6380 | |
| | Delta | | 1.864 | 1.834 | | −927 | −905 | |
| 2 | High CCT | HSH | 3.087 | 3.009 | 2.937 | 6444 | 6224 | 5992 |
| | Small S/P Spread | HSL | 2.145 | 2.128 | 2.117 | 6706 | 6588 | 6434 |
| | Delta | | 0.942 | 0.881 | 0.820 | −262 | −364 | −442 |
| 3 | Low CCT | LWH | 2.610 | 2.599 | | 2389 | 2373 | |
| | Wide S/P Spread | LWL | 1.222 | 1.239 | | 3109 | 3149 | |
| | Delta | | 1.388 | 1.36 | | 714 | −776 | |
| 4 | Low CCT | LSH | 2.098 | 2.073 | | 2713 | 2688 | |

Lighting Measurements:

Throughout the testing procedure, lighting measurements were taken to ensure that light level and color consistency was maintained for each testing condition using a Gigahertz Model # BTS256-E BiTec Sensor Luxmeter. The meter was positioned to measure the vertical illumination at the eye in the Direction of Gaze (DOG illuminance), as well as the Spectral Power Distributions received at the eye. The S/P value was calculated from the measured SPD for each lighting measurement taken. The meter provided output data into a computer file that recorded the measurements for all tests, and these measurements were reviewed for each subject and for each test.

In some cases, the results of the light measurements showed departures from the constant value desired, including some cases where the recorded value was zero. During the data analysis, some subject's data did not meet the consistency required (constant DOG illuminance or S/P values, for instance), and those subjects were consequently excluded from the analysis. The consistency for constant illuminance and S/P values for the experiments was reviewed for both within and between subject analyses. The design of the test with regard to the lighting measurements was considered critical to ensure that the subjective judgments reported by the subjects was in fact based on the lighting values that were programmed into the lighting control system.

Subject Selection:

Subjects were volunteer Musco employees or their family members who satisfied general and normal visual behaviors but were rejected if such conditions as ocular disease, color blindness, or tinted contact lenses were present. In addition, qualified subjects were not medicated regularly with pain reducers, especially opiates, and were over the age of 18 years. They were also briefly tested with an infrared pupilometer for a normal pupil response to changes in light level and were rejected if that was not the case. Those chosen were essentially naïve with no special knowledge of lighting and were unaware of the study purpose. A total of 57 subjects were tested. The distribution of these subjects is divided between three age groups as follows:

Age 18-30: 19 subjects
Age 31-50: 21 subjects
Age 51 & over: 17 subjects

The analysis of these subjects required that they completed testing for all conditions for each of the tests, 1) Brightness Comparison (BC); 2) Pupil Size (PS); and 3) Brightness Matching (BM), the latter being a separate study described in a separate paper. Due to some equipment errors in reading lighting measurements and/or obtaining pupil size data, the total number of subjects analyzed for each test varies. The total number of subjects analyzed for each test, by age group, and based on having complete data is as follows in

TABLE 3

Summary of Subjects in final analysis, by age group
TEST 1: Brightness Comparison (BC) Study:

| Subject Age Group | BC Test | PS Test | BM Test |
|---|---|---|---|
| Age 18-30 | 17 | 14 | 16 |
| Age 31-50 | 16 | 13 | 12 |
| Age 51 & over | 14 | 13 | 12 |
| TOTAL No. of | 47 | 40 | 40 |

General:

For this study, all nine conditions shown in Table 2 were tested. All four metameric pairs were tested at 60 and 150 DOG lux, and one metameric pair (Pair 2) was examined at a much higher level of 400 Lux. The purpose of this latter test was to examine comparisons at a sufficiently high illuminance level where similarity of results would reasonably assure the absence of possible rod receptor effects. The comparisons were portioned by light level into these three illuminance categories. The 4 metamer comparisons in the 60 and 150 Lux conditions were presented in randomized order between subjects in each illuminance category. Subjects were informed that the lighting would be switched back and forth between 2 scenes and they would be asked to indicate which of the 2 scenes appeared brighter.

Protocol:

Each subject was adapted to the first condition in each of the categories for a period of 2 minutes focusing on the iPad mini. Subsequently the two viewed scenes are alternated with the viewing time for each scene totaling the sum of the Transition Interval of 1 second and an Observation/Decision Interval of 5 seconds for a total time of 6 seconds. Each time the scene was presented, the experimenter called out the scene as "A" or "B", and after 3 repetitions of each pair, the experimenter asked the subject to report which one is brighter recording the subject's decision in the computer. Subjects were not allowed the choice of "No Difference".

This resulted in an approximate total time for a given subject for each pair as 6 seconds×6 presentations)+a few seconds decision time totaling about 1 minute.

Light measurements for each subject were made during the initial 2-minute adaptation period (condition A), and then once again during the $3^{rd}$ presentation of condition B, just before the subject made their final decision. The decision was recorded as 'A' or 'B'. The experimenter was not informed of which metamer was being presented during any of the tests other than the names 'A' or 'B'.

TEST 3: Pupil Size Determinations:

General:

Since it had already been established that melanopsin stimulation is a significant factor in controlling pupil size [McDougal &Gamlin (2010), Vienot (2010), Tsujimura (2010)] it was reasonable to expect that there could be pupil size differences associated with the different metamers. The earlier studies on brightness perception mentioned above did not measure pupil size as a companion to the brightness perceptions but did show that lighting spectra with higher S/P (or melanopsin content) were perceived as brighter. By present understanding these brightness perceptions would be associated with smaller pupils and therefore less retinal illuminance, but nevertheless perceived as brighter. Thus, in order to fulfill the original study objectives, potential pupil size differences were examined. This was accomplished by employing an ISCAN infrared pupilometer.

Protocol:

In order to shorten the subject time and to answer the question of associated pupil size differences it was deemed sufficient to examine pupil responses at the 150 Lux condition with the following 4 comparisons.

Pair 2, Low S/P, 150 Lux
Pair 2, High S/P, 150 Lux
Pair 1, Low S/P, 150 Lux
Pair 1, High S/P, 150 Lux The following protocol was followed for each of the lighting conditions tested:

A 3-minute adaptation time was provided for each metamer prior to recording pupil diameter data. The subject was then instructed to maintain his/her gaze at the iPad. The experimenter also recorded the light measurements from the Gigahertz light meter during this adaptation time. After adaptation time was completed, pupil diameter data was recorded for 30 seconds. The experimenter then switched the lighting to the next lighting condition and repeated the process.

When these 4 tests were completed the experimenter closed the session. The data collected for later analysis of pupil size behavior consisted of a continuous 10-second blink free sample from each 30-second pupilometer readings.

Results:

Data Output and Analysis:

Two computer data files were produced for each subject, one which was custom-programmed software that captured the data from the Gigahertz light meter for all steps of the testing, and the other that captured the pupilometry data from the ISCAN pupilometer. Both files for each subject provided output in a standard format such that a third independently written Subject File program for data collation was developed, which imported each of these two files and provided a summary of the data in a more usable format.

The data for each subject was scrutinized to determine if any of the recorded light levels or S/P values were out-of-bounds relative to the constant values in Table 2 for the BC and also for the follow-on BM tests. The Subject File also automatically determined if there was a valid 10-second section of pupilometry for each subject. This data inspection provided the necessary step to determine what, if any, data could not be used on account of unanticipated lighting changes that occurred during the test. Furthermore, if the recorded light measurements were some value that was not consistent with the test parameters, those results could not be attributed to the test conditions and thus that data was considered unreliable and not usable.

The results of the data analysis concluded that occasionally there were some failures of equipment or a light level was not recorded resulting in incomplete or not verifiable data. The following criteria were adopted as a pre-condition for excluding that data.

Exclusions for the BC test:
Either preset A or B inadvertently records a zero illuminance value
Preset A or B was significantly different than the reference light level (60, 150 or 400 lux)
Any measured S/P value differed from the programmed value by 0.05 or greater.
Exclusions for Pupilometry:
Pupilometry data is excluded for those cases where BC and BM data is excluded.
The measured light level and/or S/P value was significantly different than the correlating measured light levels employed for the follow-on BM measured values.

The test over all conditions confirmed that there is an effect of the S/P ratio difference. The higher S/P source was perceived as the brighter source in 375 of the 423 runs. The unbiased estimate of the probability is 88.5%±1.5% (n=# brighter, N=total # of runs, mean=(n+1)/(N+2), SE=√[n+1)(N+1-n)/(N+2)(N+3)^2]). The probability that the true mean is 50% is on the order of $10^{-135}$, so the main hypothesis that the S/P ratio affects brightness is confirmed in this study.

The results were highly significant for all age groups and somewhat unexpectedly the oldest group had a somewhat higher percentage in favor of the higher S/P spectrum. As mentioned, testing was also performed at a high value of 400 vertical Lux where similar results were obtained lending assurance to the conclusion that the measured effects were unlikely due to possible rod receptor transients. The summary of results is listed in Table 4.

The variability of both S/P and illuminance over the various subject runs was very low. The maximum variation in S/P within a run was 5%, and the standard deviation of the S/P values for the runs averaged 1%. These variations are small relative to the differences in S/P between sources.

The maximum variation of the illuminances was under 4%. The average DOG illuminance for the low S/P source in each run was 0.3% higher than that of the higher S/P source. The higher S/P source had a higher photopic illuminance in only 21% of the runs, and the worst-case excess was only 1.9% (1.1 lux at 59 lux). These results are in the opposite direction of the hypothesis, and therefore do not represent the presence of a confounding condition.

TABLE 4

Summary results from the Brightness Comparison (BC) Test.

| Summary Findings | | Brightness Comparison Results for 47 Subjects % of Subjects [selecting] higher S/P lighting as brighter | | | | | | | | |
|---|---|---|---|---|---|---|---|---|---|---|
| BC Test | High S/P | 3.069 | 3.039 | 3.041 | 2.086 | 2.064 | 3.938 | 3.938 | 2.599 | 2.582 |
| | Low S/P | 2.134 | 2.117 | 2.111 | 1.346 | 1.352 | 2.077 | 2.058 | 1.217 | 1.233 |
| | Delta S/P | 0.935 | 0.922 | 0.930 | 0.740 | 0.712 | 1.861 | 1.880 | 1.382 | 1.348 |

| Age Group | Qty | Avg Across Tests | HS-60 | HS-150 | HS-450 | LS-60 | LS-150 | HW-60 | HW-150 | LW-60 | LW-150 |
|---|---|---|---|---|---|---|---|---|---|---|---|
| 18-30 | 17 | 84% | 65% | 76% | 82% | 88% | 94% | 76% | 88% | 88% | 94% |
| 31-50 | 16 | 91% | 81% | 81% | 88% | 94% | 100% | 94% | 94% | 88% | 100% |
| 51-Older | 14 | 92% | 86% | 93% | 93% | 93% | 93% | 79% | 93% | 100% | 100% |
| Total | 47 | 89% | 76.6% | 83.0% | 87.2% | 91.5% | 95.7% | 83.0% | 91.5% | 91.5% | 97.9% |
| Ave for both light levels | | | 79.8% | | | 93.6% | | 87.2% | | 94.7% | |

A continuous 10 second blink free period of pupilometer data could not be found.
The result of applying these exclusions provided valid data for 47 subjects for the BC tests and 40 subjects for the pupilometry measurements.
Brightness Comparison Summary:
The dependent variable in the brightness comparison study is the frequency with which the higher S/P source was chosen as brighter in comparison with the lower S/P source. There were a total of 423 runs, spread over the 9 conditions shown in table 2, and over 3 age groups: 18-30, 31-50 and 51 and older. The number of subjects in each age group was 17, 16 and 14 respectively. The results can be analyzed in terms of the entire population, and as a function of the ratio of the S/P ratios, the illuminance at the eye, and the age of the subjects.

Because of the methodology used to construct the metamers for the low and high CCT values it was not possible to perform unbiased estimation of the effect of CCT in the brightness comparisons.
Pupil Size Results Summary:
Pupil sizes were successfully measured for 40 of the 47 subjects that completed the BC tests for the 4 conditions at 150 Lux. For the wide spread in S/P values (ratio H/L=1.91) 37 of the 40 subjects showed smaller pupils for the higher S/P value and for the small spread (S/P=1.44) 32 subjects showed smaller pupils for the higher S/P value. On average these results confirm those of other pupil size measurements Berman et al (1992), MacDougal & Gamlin (2010), Tsujimura et al (2010), Vienot (2010) and further demonstrate that pupil size is affected by the S/P or melanopic content of the viewed spectrum. These results also show that even though the photopic retinal illuminance is lower for the higher S/P spectrum (because of the smaller pupil size) the higher S/P spectrum is perceived as brighter.

Discussion:

For the conditions of the simulated athletic field with approximately ¼ of the complete visual field lit, reliable data from 47 subjects of ages ranging from 18 years to 60 years clearly showed a very significant and unequivocal effect on perceived brightness. They had a total of 423 opportunities to compare whitish metameric lightings of different spectral content and chose the spectra of higher S/P (or higher melanopic) content to be perceived as brighter 88% of the time even though the photopic illuminance at the eye was unchanged. The metamerism provided by the use of the Stockman-Sharpe cone spectral sensitivities along with the application of the Cohen & Kappauf methodology allowed for the construction of many whitish metamers with nearly undetectable color differences by most subjects. In this manner, the possibility of color confounds in the comparisons that might have occurred in other studies such as Royer &Houser (2012), especially when the difference in S/P values is small, have been greatly reduced.

Our results clearly demonstrate that for whitish lighting and when the lit field of view is extra-foveal, photopic illuminance is not the unique predictor of perceived brightness and that spectral content as described by the S/P value is also a necessary descriptor. Furthermore, these results obtained under the modified conditions here, both compliment and extend the earlier results of Berman et al (1990) and Brown et al (2012). To the extent that the metamerism employed here is accurate, the comparisons evaluated are based on identical cone stimulation and thus the judgment differences cannot be associated with the predominance of any single cone receptor response such as an S-cone effect.

Figure 10I:
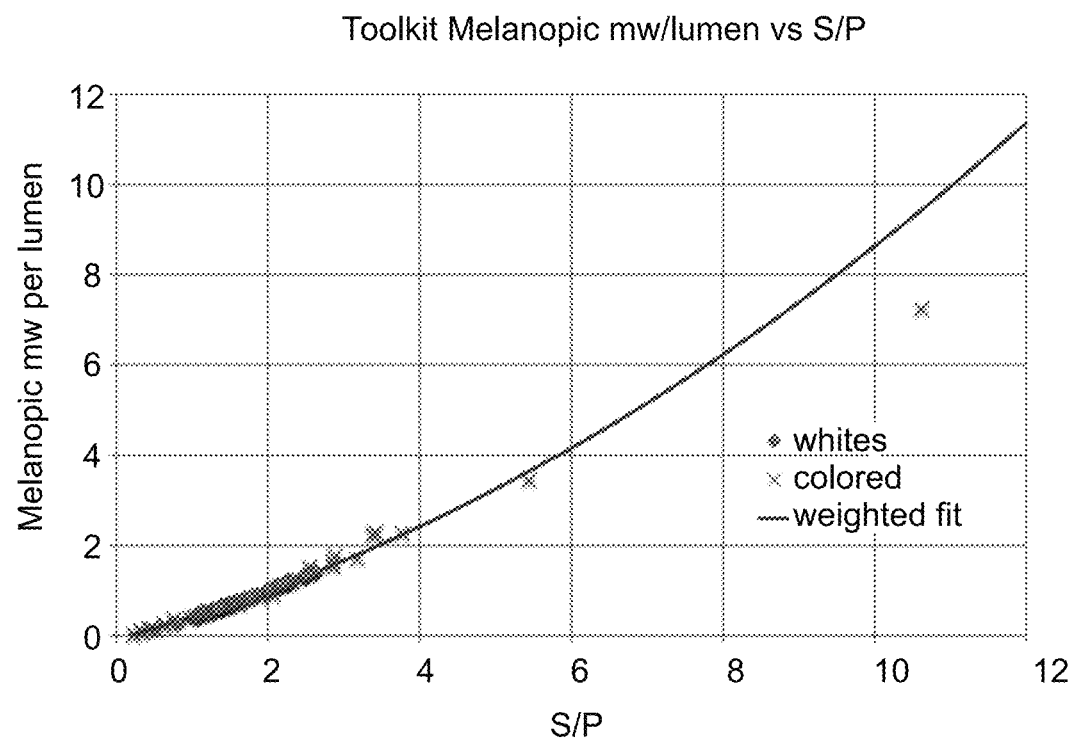

Presumably the underlying mechanism for the brightness perceptions is the result of the action of the retinal melanopsin receptors (Hattar et al 2002) whose spectral behavior when stimulated by polychromatic light sources is highly correlated with the ratio of scotopic to photopic S/P content of those sources [Berman (2008), Berman & Clear (2008, 2014)] thus allowing the S/P value as a marker of melanopic content. This high degree of correlation is shown in FIG. 10I below taken from Berman & Clear (2014). FIG. 10I relates to the following: Melanopic/lumen vs S/P Correlation: This graph shows the correlation between melanopic sensitivity and S/P value based on the spectral power distributions of a sample of 60 "white" light sources, and 28 color sources such as monitor colors. The S/P ratios of the whites ranged from 0.81 (a low color temperature high pressure mercury) to 2.62 (7500° K fluorescent lamp), while the S/P ratios for colors ranged from 0.23 (low pressure sodium) to 10.6 (LED monitor color blue). The fitted equation with a 99.4% correlation is given by Melanopic mw/photopic lumen (Mmw/P)=(0.041212*S/P+0.45827)*S/P–0.07 428 Range: 10.7>S/P>0.22. Melanopic content is based on the melanopic sensitivity function, Lucas et al (2014), and given in the Tool Kit website.

The perceived brightness differences of this study are observed in a very short exposure time of a few seconds thereby reducing the dependence on memory load. Because of the switching protocol employed and the vagaries of memory, any accurate estimation of the longtime stability of these brightness perceptions is essentially precluded. If melanopsin receptors are the underlying mechanism Do et al (2010) then the action time of the stimulating retinal pathways would be much shorter than the time course associated with the post illumination pupil response (PIPR) claimed as elucidating the typical response time for melanopsin receptors (McDougal& Gamlin, 2010). To the extent that our metamers are veridical and that rod receptors are not the underlying mechanism, our results indicate the likelihood of a rapid melanopic related response Peirson et al (2009).

The potential practical and economic consequences for lighting engineering that relate to the magnitude of this brightness effect are evaluated in the follow-on study of brightness matching.

REFERENCES

Bailes H J, Lucas R J. (2010). Melanopsin and inner retinal photoreception. *Cellular and Molecular Life Sciences,* 67(1), 99-111.

Berman S M, Jewett D L, Fein G, Saika G, Ashford F. (1990), Photopic luminance does not always predict perceived room brightness. Lighting Research and Technology 1990; 22: 37-41.

Berman, S. M., G. Fein, D. L. Jewett, G. Saika, and F. Ashford (1992). Spectral Determinants of Steady-State Pupil Size with Full Field of View. *Journal of the Illuminating Engineering Society,* 21(2) 3-13.

Berman, S M &Clear, R D; 2008; Past vision studies can support a novel human photoreceptor, Light & EngineeringVol. 16, No. 2, pp. 88-94.

Berman, S. M; 2008, A new retinal photoreceptor should affect lighting practice Lighting Research and Technology; 40; 373.

Berman, S M & Clear, R D (2014) Implications of the Relationship between S/P and Melanopic Efficiency: Illum Eng. Soc Conference report November 2014

Boynton R M. (1996) *J Opt Soc Am A Opt Image Sci Vis.* August; 13(8):1609-21. Frederic Ives Medal paper. History and current status of a physiologically based system of photometry and colorimetry.

Brown T M, et al. (2012) Melanopsin-based brightness discrimination in mice and humans. CurrBiol 22(12): 1134-1141.

CIE (2006) Fundamental chromaticity diagram with physiological axes—Part 1 Technical Report 170-1.

Cohen, J B and Kappauf, W E, (1982) Metameric color stimuli, fundamental metamers, and Wyszecki's metameric blacks. *The American Journal of Psychology* 95(4):537-64.

Cohen, J B and Kappauf, W E (1985), "Color mixture and fundamental metamers: Theory, algebra, geometry, application", American Journal of Psychology. 1985 Vol. 98, No 2, pp. 171-259.

Do M T, Yau K W (2010) Intrinsically photosensitive retinal ganglion cells. Physiol Rev 90(4):1547-1581.

Ecker J L, et al. (2010) Melanopsin-expressing retinal ganglion-cell photoreceptors: Cellular diversity and role in pattern vision. Neuron 67(1):49-60.

Harrington, R. E. (1954). Effect of color temperature on apparent brightness. J. Opt. Soc Hattar S, et al (2002) Melanopsin-containing retinal ganglion cells: Architecture, projections, and intrinsic photosensitivity. Science 295(5557):1065-1070.

Lucas, R., Lall, G., Allen, A. & Brown, T (2012). How rod, cone, and melanopsin photoreceptors come together to enlighten the mammalian circadian clock. *Prog Brain Res,* 199, 1-18.

Lucas R J, Peirson S N, Berson D M, Brown T M, Cooper H M, Czeisler C A, Figueiro M G, Gamlin P D, Lockley S W, O'Hagan J B, Price L L A, Provencio I, Skene D J, Brainard G C (2014) Measuring and using light in the melanopsin age. Trends in Neurosciences 37:1-9.

McDougal, D. H. & Gamlin, P. D. 2010 The influence of intrinsically-photosensitive retinal ganglion cells on the spectral sensitivity and response dynamics of the human pupillary light reflex. Vision Res. 50, 72-87.

Peirson S N, Halford S, Foster R G (2009) The evolution of irradiance detection: Melanopsin and the non-visual opsins. Philos Trans R Soc Lond B BiolSci 364(1531): 2849-2865.

Royer M P & Houser K W, (2012) Spatial Brightness Perception of Trichromatic Stimuli: LeukosVol 9, No2, (October) pp. 89-108

Shaw, Mark Q, (1999), Evaluating the 1931 CIE Color Matching Functions: A thesis submitted in partial fulfillment of the requirements for the degree of Master of Science in Color Science in the Center of Imaging Science, Rochester Institute of Technology June 1999

Stockman, A., & Sharpe, L. T. (1999). *Cone spectral sensitivities and color matching*. In K. Gegenfurtner& L. T. Sharpe (Eds.), *Color vision: From Genes to Perception* (pp. 53-87) Cambridge: Cambridge University Press.

Stockman, A. and Sharpe, L. T. (2000) *Spectral sensitivities of the middle-and long-wavelength sensitive cones derived from measurements in observers of known genotype. Vision Research*, 40, 1711-1737.

Stockman, A., & Sharpe, L. T. (2006). *Physiologically-based colour matching functions*. In *Proceedings of the ISCC/CIE Expert Symposium '06: 75 Years of the CIE Standard Colorimetric Observer* (pp. 13-20). Vienna: CIE Central Bureau.

Tool Kit:

http://lucasgroup.lab.ls.manchester.ac.uk/research/measuringmelanopicil luminance/Tsujimura S, et al (2010) Contribution of human melanopsin retinal ganglion cells to steady-state pupil responses. Proc BiolSci 277 (1693):2485-2492.

Vienot, F. (2010) The effect of controlled photopigment excitations on pupil aperture. Ophthal Physiol. Opt 30: 484-491.

Vienot, F et al., (2012) "Domain of metamers exciting intrinsically photosensitive retinal ganglion cells (ip-RGCs) and rods", Journal of Optical Society of America A, February 2012, Vol 29, No 2, pp. A366-A376.

E. IES #2 (Supplemental Information)

Brightness matching determines the trade-off between S/P values and illuminance level.

Bradley Schlesselman, Myron Gordin, Larry Boxler[1], Jason Schutz, Sam Berman[2], Brian Liebel[2], Robert Clear[2]

Musco Sports Lighting, LLC, 100 1$^{st}$ Avenue West, Oskaloosa, Iowa 52577

Abstract:

In a previous Brightness Comparison study (BC Study, Schlesselman et al 2015), brightness perception comparisons in a simulated sports field were evaluated for photopically equal and constant color lighting (metamers) but of different melanopic content, as measured by the S/P ratio. In that study, subjects overwhelmingly judged the lighting with the higher S/P value as appearing brighter. In this companion study, 40 subjects who completed the previous study comprising the 3 age groups (18-30 years, 31-50 yrs and >50 years) sat in a chair positioned at an edge and midpoint of the simulated field, providing a binocular and unobstructed view of both the lit "field" and dark surround that simulates a real sports field. The subjects were provided with a means to adjust light levels to achieve an equality of perceived brightness. The illuminance levels were 60 and 150 vertical lux at eye level in the direction of gaze, corresponding to those measured for spectators and performers in an operating field. Subjects were Musco employees or their family that had no special knowledge in lighting and were unaware of the study purpose. The lighting utilized theatrical luminaires with multiple and different colored LED sources combined to form four pairs of metamers, each pair consisting of one metamer having a relatively higher S/P ratio compared to the other. Two pairs had relatively higher nominal CCT values than the other two pairs, and within each CCT set of metamers, one pair had a wide spread between the high and low S/P ratio metamer, while the other pair had a relatively smaller difference between the S/P ratios. The S/P values ranged approximately from 1.2 to 4 and the difference between the S/P values for a compared pair varied between 0.72 and 1.86.

The conventional CCT values ranged from nominal 2700K to 6700K. In order to achieve a condition of equal brightness perception, subjects were given repeated opportunities to adjust the level of one of the lighting conditions within a given metameric pair (randomly selected as the high S/P or low S/P source) by raising or lowering the light level with a manual dimming control slider to select a level where the 2 lightings appeared equally bright. This test was performed at two light levels (60 &150 Lux) for each of the four metameric pairs. In this test, 92% of the 40 subjects chose to lower the photopic level of the higher S/P lighting to obtain an equality of brightness perception. Overall, the high S/P source was set to a lower light level than the low S/P source 293 times out of 320 runs, which has a probability of $10^{-151}$ of occurring by chance.

The amount of light level reduction was determined leading to an augmentation of the dependence of brightness perception on photopic illuminance P by the factor $P(S/P)^n$ The exponent n was empirically determined from the data as n=0.436±0.017.

The role of conventional CCT within each metameric pair was also examined and it was shown that there was no statistically significant effect.

In terms of practical applications for lighting engineering, these results show that substantial energy savings can be achieved by replacing sources with relatively low S/P values with e.g. LED sources capable of higher S/P values while maintaining the same brightness perception even in a nighttime environment where only a fraction of the visual field is lighted. For example, replacement in a lighted athletic field employing a typical MH source of S/P=1.4 by a LED source of S/P=2.4 would lead to the possibility of a 25% light level reduction based on the principle of equal perceived brightness. This feature is of sufficient magnitude that it should be a design consideration for sports lighting applications.

Background:

Previous studies Berman et al (1990), Brown et al (2012), Royer &Houser (2012) have shown that in conditions of full field of view lightings of the same color but of different spectral content and also with equal photopic luminance (metamers) are not perceived as equally bright. Current understanding of these observations [Brown et al (2012), Ecker et al, (2010), Lucas et al 2014] is that they are likely a result of the responses of non-image forming melanopsin photoreceptor widely distributed in the retina of the eye and whose spectral responses are not included in the determination of photopic luminance. Thus, it is reasonable to expect that there could be a trade-off between melanopic content and photopic light level to achieve a given level of brightness perception. The quantitative aspect of this trade-off was not examined in the previous studies and as such is the primary objective of the present study.

Methods:

The testing took place in the same room as the BC study of brightness comparisons (Schlesselman et al 2015). The simulated sports field was constructed inside a large hall and had the dimensions of 30 by 20 feet (width and length). To simulate a realistic sports lighting situation, it was lit so that about ¾ of the visual solid angle was in the dark from the perspective of the subject situated at the midpoint of the longer dimension and at the front end of the shorter dimension. FIGS. 10A, 10B and 10C show a perspective view of the simulated field construction, a cross-sectional drawing, and a photograph, respectively, of the test environment. The simulation of the field was accomplished by lighting only the lit portion of the test floor, which was painted a spectrally neutral matte gray color and had an incline of 7.5 degrees to establish concordance in the end point viewing angle of the subject as would occur on the real field. The dark portion was obtained by using matt black fabric that was placed to surround the lit portion of the test space.

Achieving the necessary illuminance at the subject's eye required both direct lighting on the test field floor plane to yield a field luminance distribution approximating that of the real sports field, along with the addition of several overhead fixtures that provided the majority of vertical illuminance at the observer eye that would come from typical high mast sports lighting luminaires in real conditions. Attention was paid to assure that these overhead fixtures were not directly visible by the subject as well as to minimizing possible direct glare due to the proximity of these overhead fixtures in relation to the subject position (see FIG. 10D).

For the study, subjects sat in a chair at the midpoint of the long dimension at the edge of the lit floor as seen in FIG. 10C and viewed an iPad Mini tablet placed in line with center of the long dimension and at the middle of the lit floor. The iPad screen subtended essentially a foveal visual angle of about 3 degrees from the subject position and provided a fixation point. The iPad was set to display slow temporal screen variations by showing a simulated lava lamp scene of fixed color thereby helping to reduce boredom and to assure that the direction of gaze would be similar for all subjects. The iPad was placed in the center of a 12 inch diameter black circle (FIGS. 10C and 10D) and together these essentially foveal objects help to minimize the transient 'Maxwell Spots' that can be sensed in the central visual field when switching between test metamers and when the lit field of view extends much beyond the fovea.

The lighting system and the construction of the metamers are the same as in our previous study (Schlesselman et al 2015) and are described in detail there. As in our previous study achieving equal color of the compared lightings is obtained by assuring equal excitation of the 3 retinal cones accomplished through employing the Stockman cone fundamentals (Stockman et al 1999,2000,2006, CIE 2006) and not by equality of the CIE tristimulus values. Metamers are constructed using the methods described by Cohen & Kappauf (1982,1985) and Vienot et al (2012)

The same 7 LED sources and 4 metameric pairs as employed in the previous study are also used for this study. The CIE chromaticity values of these metamers are shown graphically in FIG. 10F below along with their spectral power distributions in FIG. 10H.

TABLE 5

Lighting Conditions: Vertical DOG Illuminance, S/P values and CCT values.

| | | | Illuminance Levels | | | Illuminance Levels | | |
|---|---|---|---|---|---|---|---|---|
| Pair | Description | Code | 60 S/P | 150 S/P | 400 S/P | 60 CCT | 150 CCT | 400 CCT |
| 1 | High CCT Wide S/P Spread | HWH HWL | 3.952 2.088 | 3.898 2.064 | | 5653 6580 | 5475 6380 | |
| | Delta | | 1.864 | 1.834 | | −927 | −905 | |
| 2 | High CCT Small S/P Spread | HSH HSL | 3.087 2.145 | 3.009 2.128 | 2.937 2.117 | 6444 6706 | 6224 6588 | 5992 6434 |
| | Delta | | 0.942 | 0.881 | 0.820 | −262 | −364 | −442 |
| 3 | Low CCT Wide S/P Spread | LWH LWL | 2.610 1.222 | 2.599 1.239 | | 2389 3109 | 2373 3149 | |
| | Delta | | 1.388 | 1.36 | | 714 | −776 | |
| 4 | Low CCT Small S/P Spread | LSH LSL | 2.098 1.352 | 2.073 1.356 | | 2713 3040 | 2688 3054 | |
| | Delta | | 0.746 | 0.717 | | −327 | −366 | |

Lighting Measurements:

Throughout the testing procedure, lighting measurements were taken to ensure that light level and color consistency was maintained for each test. The light meter (Gigahertz Model # BTS256-E BiTec Sensor Luxmeter) also recorded the final light level reading for the matched brightness condition and provided the necessary readings to ensure that color consistency was maintained while the light sources were being dimmed. The meter was a positioned to measure the vertical illumination at the eye in the Direction of Gaze (DOG illuminance), as well as the Spectral Power Distribution curves received at the eye. The S/P value was calculated from the measured SPD for each lighting measurement taken. The same meter provided output data into a computer file that recorded the measurements for all tests, and these measurements were reviewed for each subject and for each test.

Subjects:

The same subjects as those who participated in the previous Brightness Comparison study participated in the brightness matching.

A total of 40 subjects completed the brightness matching with 16 in the younger than 30 years, and 12 each in the other 2 age groups.

Brightness Matching

Protocols: General:

Employing the same set of lighting conditions as in the BC study, subjects were given a manual slider control whose purpose was to adjust the light level of the 'B' condition to match the fixed 'A' lighting condition of the BC testing. Subjects were instructed to adjust the slider so that the 2 scenes would appear equally bright.

Specific Protocol:

To implement the matching the experimenter instructed the subject to move the slider to adjust light intensity of Scene B to match the brightness of Scene A (fixed) until the subject judged the two scenes to be equal in brightness. The scene of fixed illuminance was randomly chosen as either the high or low S/P condition. The subject was allowed to ask the experimenter to switch back and forth between scenes in order that they can further adjust the light level as many times as they wanted. Subjects were told to try to judge equivalency in a short time period following switching (close to 1 second, no longer than 5 seconds). After achieving equivalent brightness, the experimenter presents each scene for 5 seconds to confirm the equal brightness setting with the subject. The subject was allowed final tweaking if they change their mind after viewing the conditions under a longer exposure. The experimenter recorded the resulting DOG illuminance equivalency level with appropriate button push.

This process was repeated for each of the seven remaining pairs, with a 30 second adaptation time between each new pair within the light level, a five minute break between the light level changes from 60 to 150 Lux (between test 4 and 5). The subject time to accomplish this was approximately 30 minutes at most. Light measurements were recorded for each subject and for each condition.

Brightness Matching (BM) Results:

This test employed the same set of conditions as for the BC testing except the 400 Lux condition was not used due to the limitations of the light sources. Thus, there were 8 different conditions (4 at 60 Lux and 4 at 150 Lux) as shown in Table 5 above. Thirty-nine of the 40 subjects were the same as those that participated in the BC study and the one additional subject was an excluded subject in the BC testing because of a failure to record the light levels.

Not all subjects chose a lower illuminance for the higher S/P source, and this reversal was more pronounced when the difference in S/P ratios between the two metamers were close. However, even in the worst cases (HS-60 and HS-150), 33 out 40 subjects used a lower illuminance for the high S/P source. The probability of this occurring by chance is 0.002%. For the wide spread in S/P values the worst case was 37 out of 40 and the best case was 40 out of 40. Thus, there was a clear indication that the higher S/P sources required less illuminance to achieve the perceived brightness of the lower S/P sources. The summary of results is given below in Table 6.

levels at the eye; 60 and 150 lux, and 4 different sets of S/P ratios. An attempt was made to extend the illuminance range to 400 lux, but the apparatus did not have a sufficient illuminance range to allow brightness matches for all subjects, so this attempt was aborted, and the 400 lux data was dropped from further analysis. The subjects were grouped into age groups as in the study of brightness comparison, with the number in the age groups being 16, 12, and 12, respectively.

The average ratio of S/P values over the two sources for the eight runs ranged from 1.44 to 2.13. The maximum deviation from the average ratio within a run was two percent. The dependent variable in the brightness matching experiment i.e. the ratio of photopic illuminances for equal brightness perception, is a continuous variable, and is amenable to least squares fitting. We found that the fit to S/P ratios explains more of the variance than a fit to CCT (as computed in the standard XYZ space), and is therefore the preferred explanation for the results. We lastly show that there appears to be no interaction between S/P and CCT in these metameric matches.

The BC Study (Schlesselman, 2015) showed that subjects chose the high S/P source as being brighter than the low S/P of the same illuminance at the eye at a statistically significant level. In this Brightness Matching (BM) test this should translate into subjects choosing a lower illuminance at the eye for the high S/P source than for the low S/P source. With 8 runs for each subject, 32 of the 40 subjects chose a lower illuminance for the high S/P source than the low S/P source at a statistically significant level (7 out of 8 runs). Only one subject showed no preference (4/8). When averaged over subjects, the worst cases were for the two runs where the S/P ratio for the high to low S/P source was 1.44. Even for these two runs, 33 out of 40 subjects had a positive result (P=0.002%). Overall, the high S/P source was set to a lower

TABLE 6

Summary results from the Brightness Matching (BM) Test.

| Summary Findings | | | Brightness Matching Results for 40 Subjects % of Subjects selecting lower illuminance for high S/P lighting | | | | | | | |
|---|---|---|---|---|---|---|---|---|---|---|
| BM Test | | High S/P | 3.078 | 3.044 | 2.087 | 2.064 | 3.938 | 3.938 | 2.599 | 2.582 |
| | | Low S/P | 2.133 | 2.117 | 1.347 | 1.352 | 2.077 | 2.058 | 1.217 | 1.233 |
| | | Delta S/P | 0.945 | 0.927 | 0.740 | 0.712 | 1.861 | 1.880 | 1.382 | 1.348 |

| Age Group | Qty | Avg Across Tests | HS-60 | HS-150 | LS-60 | LS-150 | HW-60 | HW-150 | LW-60 | LW-150 |
|---|---|---|---|---|---|---|---|---|---|---|
| 18-30 | 16 | 87% | 69% | 63% | 88% | 88% | 94% | 94% | 100% | 100% |
| 31-50 | 12 | 83% | 83% | 92% | 100% | 92% | 83% | 92% | 100% | 100% |
| 51-Older | 12 | 97% | 100% | 100% | 83% | 100% | 100% | 100% | 92% | 100% |
| Total | 40 | 92% | 82.5% | 82.5% | 90.0% | 92.5% | 92.5% | 95.0% | 97.5% | 100.0% |
| Ave for both light levels | | | 79.8% | | 93.6% | | 87.2% | | 94.7% | |
| | | | Ave. Light Level Reduction (% Using Low S/P as base) | | | | | | | |
| Ave. Reduction Percentage (Using Low S/P as base) | | | 14.3% | 11.7% | 13.6% | 15.1% | 20.7% | 25.1% | 27.3% | 27.9% |
| Ave for both light levels | | | 13.0% | | 14.3% | | 22.9% | | 27.6% | |

Statistical Analysis of Brightness Matching Study:

Forty subjects adjusted the brightness of a test light to match the brightness of a reference light. The lights were metameric in color, but differed in their S/P ratios. Each subject did 8 matches covering 2 reference illuminance light level than the low S/P source 293 times out of 320 runs, which has a probability of $10^{-151}$ of happening if the true probability was 50%.

Thirty-nine of the 40 subjects in the brightness matching study also had complete data for the BC study with the same sets of reference conditions. A comparison of the two studies highlights the variability of the results in the BC study. Of the 312 matching runs in the BC study, 26 of them had a negative result in that the low S/P source was judged brighter than the high S/P source. In the equivalent brightness matching experiment, only 9 of these conditions resulted in a negative result brightness match requiring a higher lux level with the high S/P source. The BC results did predict a difference in the average brightness matching illuminances. The 26 conditions with a negative brightness comparison had an average illuminance ratio of the low S/P source to the high S/P source of 1.036 (which is a slightly positive result). The 286 runs with a positive brightness comparison had an illuminance ratio of 1.29 on the brightness match, which is a strongly positive result.

A Model for Brightness Perception:

The main point of the BM study, other than demonstrating that there was an effect, was to identify the S/P exponent in the simple model of brightness dependence, i.e., $$\log B = \text{const} \times \log[P(S/P)^n] = \text{const} \times \log B_{br}$$

where the "brightness lumen", $B_{br}$, has the simple form: $B_{br} = P \times (S/P)^n$.

In the BM study, the brightness of the reference source, $B_1$, is adjusted to achieve equal brightness of the test source, $B_2$. If we let $r=S/P$, then the log of the ratio of the illuminances is equal to a constant, n, times the log of the ratio of the S/P ratios: $\log(P_1/P_2) = n \log(r_1/r_2)$. A least-squares fit for n gives the value $n=0.436\pm0.017$.

This result is the principal quantitative determination for the BM testing.

The exponent is slightly smaller but reasonably close to that determined in the earlier study of Berman et al (1990) carried out in conditions where the full field of view was illuminated and where the exponent was determined there roughly as 0.5.

The age of the subject was close to significant in the BC study. We tested for an interaction of age and brightness exponent. Although the trend of the younger subjects appearing to have a lower exponent, the result was not statistically significant at the P=30% level. However, a similar test for the interaction of subject and exponent was significant at the P<0.01% level. Adding a subject interaction term increases the amount of variance explained by the fit from 17% to 47%, and slightly reduces the standard error of the exponent to 0.015. Subject exponents ranged from 0.061 to 0.0.922, and had a standard deviation about the mean of 0.185. Note the standard deviation appears to reflect a real variation in sensitivity to the S/P ratio among subjects.

The S/P value was also statistically significant in the BC study, but much of this effect should be caught in the analysis of the data in terms of the S/P exponent. The illuminance level was not a statistically significant effect in the brightness comparison study. Both factors are rejected in the analysis of exponent for the BM study.

Is there an effect of CCT?

We examined the possibility of there being an interaction between S/P and color temperature by looking for a difference in the calculated S/P exponent in the high CCT versus the low CCT tests. A within subject comparison matching the illuminances, and the rough S/P ratios gave 160 differences between the high and low CCT runs. The difference of high—low CCT was $0.013\pm0.034$, which is not statistically significant. We therefore rejected the hypothesis that there was an interaction between CCT and S/P in the perception of brightness in these metameric matches and conclude that there was no significant effect of CCT in the brightness matching study.

Limen Test: (Testing Subject Discerning Ability to Match Brightness) Description:

The purpose of the limen test was 2-fold; the first is as a check that the equipment is functioning properly and second to evaluate the discerning ability level of the group of 40 subjects that successfully completed the BM test. That is, how good they are at being able to state that one condition can be adjusted to appear as having an equal brightness. To assess this ability to match alternating scenes for equality in brightness perception the limen test was performed. In this case the lighting for the 2 alternating scenes had equal spectral content with a nominal S/P value of 2.12 but where a test lighting of different DOG illuminance was to be adjusted by the subject with the slider so as to appear equally bright when compared with a standard scene of fixed illuminance. For the initial condition the test lighting was either 20% higher or 20% lower than the standard scene and alternated between successive subjects. Subjects then adjusted the test illuminance level with the slider until there was a match in brightness perception. The testing was done at the 2 standard levels of 60 and 150 Lux.

The detailed protocol was essentially the same as in the BM testing and is as follows. The subject was instructed to focus on the iPad Mini and allowed adaptation to the light condition scene A, which was the baseline illuminance, for 2 minutes for each of the 2 standard levels. After this period was complete, the experimenter alternated between scenes A and B, with the subject using the slider dimmer to adjust scene B to the level they felt was equal to scene A. Scene B light level was set at an increase or decrease of 20% and with the increased or decreased value alternating with each successive subject.

The subject could ask the experimenter to switch back and forth between scene A (fixed light level) and scene B (adjustable light level), with the reminder that the subject should try to judge equivalency in a short time period following switching (close to 1 second, no longer than 5 seconds).

After achieving equal brightness perception, the experimenter presented each scene for 5 seconds and confirmed the equal brightness setting with the subject. The subject was allowed final tweaking if a final change was desired after viewing the conditions under the longer exposure. The experimenter then recorded the resulting equivalency light level with an appropriate button push.

Limen Test Results:

The mean difference in S/P of the test lighting from the reference lighting was $0.14\%\pm0.13\%$ for the 60 lux source, and $0.06\%\pm0.08\%$ for the 150 lux source. The maximum difference was 0.5% and 0.6% respectively.

One subject was unable to make a match within 70%, and was further unable to complete all of the brightness matching tests. This subject was not included in the analysis. Among the remaining subjects the maximum limen was 20%, while the overall subject mean limen was $0.7\%\pm1.2\%$ s.e. of the test illuminance. Thus, the BM study results where the selected reductions amounted to around 20% can be considered as reliable and not arbitrary resulting from testing conditions being beyond their discerning capability and we can be reasonably confident that those differences obtained in the BM testing are well within the subjects' capabilities.

Discussion:

The purpose of the brightness matching was to determine the adjusted levels of photopic illuminance that would produce perceptual equality when the S/P values were different. The data showed that for the 40 subjects with 8 different lighting conditions, they chose on average to lower the light level of the higher S/P spectrum for 92% of the trials and depending on the condition this ranged from 83% to 99%. Thus, we conclude that there is a trade-off between illuminance and S/P value, i.e. since a spectrum with a higher S/P value was perceived as brighter in the comparison study, its photopic illuminance can be lowered by an amount empirically determined that provides perceptual equality.

This result implies that there should be a quantitative relationship between a given amount of photopic illuminance difference and an associated difference in S/P value. To evaluate such a relationship the simple model introduced by Berman et al (1990) that followed on the classical luminance dependence of brightness perception was employed. In that model, brightness perception (B) would depend on luminance (P) as modified by the multiplicative factor $(S/P)^n$ where the exponent n is to be empirically determined. Since the classical luminance dependence of brightness perception is provided by a power law the inclusion of the S/P dependence is assumed to be extended by the equation $$\text{Log } B = \text{constant} \times [\text{Log } P(S/P)^n].$$

Thus if 2 spectra of different S/P values are perceived as equally bright at 2 different values of S/P then the above equation applied at equal values of B can be solved to determine a value for the exponent n.

With 8 lighting conditions and 40 subjects there were 320 opportunities to evaluate the exponent n. The analysis led to an overall exponent value of $n = 0.436 \pm 0.021$ for the entire subject group covering all 3 age categories. There was no significant effect of age.

Correlated Color Temperature (CCT) Variations:

Prior studies evaluating brightness perception found that traditionally determined higher color temperature lighting was perceived as brighter Harrington (1954). But without control of S/P those comparatively higher CCT spectra associated with polychromatic light sources will generally have comparatively higher S/P values. Our premise is that these different brightness perceptions are a result of different S/P values serving as the spectral proxy for melanopsic content (Berman 2008, Berman & Clear 2014, Brown 2012) and are not due, per se, to a pure CCT effect. In the studies performed here we attempted to examine whether there was a pure traditional (based on CIE chromaticity) CCT effect on brightness perception and in the selection of conditions traditional CCT was varied between nominal high around 6500K to low around 2700K. However, for the formation of the various metamers, we were not able to find a calculational procedure that allowed constant S/P value but different traditional CCT values as modifying CCT was always accompanied by a change in S/P under the constraint of our metamerism. This occurs because metamers constructed by employing the standard CIE procedure of equal chromaticity will have the same traditional CCT values as such metamers also have the same vector distance to the black body locus. However, as described above, the psychophysically improved metamers employed here do not have equal CIE chromaticities (see FIG. 10F) but alternatively they would have equal equivalent chromaticities in a color space based on the Stockman/Sharpe cone sensitivities. Nevertheless, in the brightness matching study where the explicit dependence of brightness perception on S/P via its exponent could be determined, it was possible to test whether the exponent had different values depending on the condition of high or low traditional CCT. This evaluation yielded a difference in the exponent of $0.013 \pm 0.034$, which is indistinguishable from zero and therefore we conclude that there is an absence of any significant traditional CCT effect on brightness perception.

Is the Protocol of Rapid Alternation Between Metamers Accounting for the Full Effect of Melanopsin Activation?

The results determined here are consistent with present understanding of melanopsin response from the point of view of an operative additional spectral sensitivity with a peak response in the bluish spectral region. The similarity of the results at three eye illuminances namely 60,150 and 400 Lux in the BC study lend support that the underlying mechanism is unlikely to be a direct response of rod receptors. On the other hand, from the psychophysical approach employed here it is not possible to conclude whether the spectral effects are a result of a subset of rapid response melanopsin cells that are directly involved in this rapidly evaluated brightness perception. Since present understanding of melanopsin temporal behavior implies a slow response (McDougal & Gamlin (2010), Bailes & Lucas (2010), Do&Yau (2010), Ecker (2010) with time periods much longer than the few seconds employed in the switching protocol it is also possible that the full tonic response to brightness perception is not fully established here. Further studies would be useful to fully elucidate this concern. Perhaps a study performed in a steady state mode utilizing dichoptic viewing with visual field spectral optics adjusted to stimulate and allow comparison of non-overlapping cortical regions associated with each eye might provide further insight.

Implications for Lighting Practice:

In terms of practical applications for lighting engineering, the results of the BM study show that substantial energy savings can be achieved by replacing typical HID sources with their relatively low S/P values with e.g. LED sources capable of much higher S/P values while maintaining the same brightness perception even in a nighttime environment where only a fraction of the visual field is lighted. For example, replacement in a lighted athletic field employing a typical MH source of S/P=1.4 by a LED source of S/P=2.4 would lead to the possibility of a 25% light level reduction (as measured with a standard light meter) based on the principle of equal perceived brightness and the exponent value of 0.436. This feature is of sufficient magnitude that it should be a design consideration for sports lighting applications.

REFERENCES

Bailes H J, Lucas R J. (2010). Melanopsin and inner retinal photoreception. *Cellular and Molecular Life Sciences,* 67(1), 99-111.

Berman S M, Jewett D L, Fein G, Saika G, Ashford F. (1990), Photopic luminance does not always predict perceived room brightness. Lighting Research and Technology 1990; 22: 37-41.

Berman, S. M; 2008, A new retinal photoreceptor should affect lighting practice Lighting Research and Technology; 40; 373.

Berman, S M & Clear, R D (2014) Implications of the Relationship between S/P and Melanopic Efficiency: Illum Eng. Soc Conference report November 2014.

Brown T M, et al. (2012) Melanopsin-based brightness discrimination in mice and humans. CurrBiol 22(12): 1134-1141.

CIE (2006) Fundamental chromaticity diagram with physiological axes—Part 1 Technical Report 170-1.

Cohen, J B and Kapp auf, W E, (1982) Metameric color stimuli, fundamental metamers, and Wyszecki's metameric blacks. *The American Journal of Psychology* 95(4):537-64.

Cohen, J B and K app au f, W E (1985), "Color mixture and fundamental metamers: Theory, algebra, geometry, application", American Journal of Psychology. 1985 Vol. 98, No 2, pp. 171-259.

Do M T, Yau K W (2010) Intrinsically photosensitive retinal ganglion cells. Physiol Rev 90(4):1547-1581.

Ecker J L, et al. (2010) Melanopsin-expressing retinal ganglion-cell photoreceptors: Cellular diversity and role in pattern vision. Neuron 67(1):49-60.

Harrington, R. E. (1954). Effect of color temperature on apparent brightness. J. Opt. Soc Lucas R J, Peirson S N, Berson D M, Brown T M, Cooper H M, Czeisler C A, Figueiro M G, Gamlin P D, Lockley S W, O'Hagan J B, Price L L A, Provencio I, Skene D J, Brainard G C (2014) Measuring and using light in the melanopsin age. Trends in Neurosciences 37:1-9.

McDougal, D. H. & Gamlin, P. D. 2010 The influence of intrinsically-photosensitive retinal ganglion cells on the spectral sensitivity and response dynamics of the human pupillary light reflex. Vision Res. 50, 72-87.

Royer M P & Houser K W, (2012) Spatial Brightness Perception of Trichromatic Stimuli: LeukosVol 9, No2, (October) pp. 89-108

Schlesselman et al (2015), Brightness judgments in a simulated sports field correlate with the S/P value of light sources. Submitted for presentation IES Conference Indianapolis, Ind.

Stockman, A., & Sharpe, L. T. (1999). *Cone spectral sensitivities and color matching*. In K. Gegenfurtner & L. T. Sharpe (Eds.), *Color vision: From Genes to Perception* (pp. 53-87) Cambridge: Cambridge University Press Stockman, A. and Sharpe, L. T. (2000) *Spectral sensitivities of the middle-and long-wavelength sensitive cones derived from measurements in observers of known genotype. Vision Research,* 40, 1711-1737.

Stockman, A., & Sharpe, L. T. (2006). *Physiologically-based colour matching functions. In Proceedings of the ISCC/CIE Expert Symposium '06: 75 Years of the CIE Standard Colorimetric Observer* (pp. 13-20). Vienna: CIE Central Bureau.

Vienot, F et al., (2012) "Domain of metamers exciting intrinsically photosensitive retinal ganglion cells (ip-RGCs) and rods", Journal of Optical Society of America A, February 2012, Vol 29, No 2, pp. A366-A376.

What is claimed is:

1. A method of illuminating an area comprising:
   a. selecting a set of light sources comprising:
      i. a first subset configured to provide higher melanopic content; and
      ii. a second subset configured to provide lower melanopic content; and
      iii. wherein the first subset and second subset of light sources are metamers and produce a white light;
   b. selectively driving the first and second subset of light sources between 0 and 100 percent duty cycle;
   c. so that the set of light sources can be used for:
      i. general lighting; and
      ii. circadian lighting; and
   d. a net perceived white color and brightness of the light sources remains constant during selective driving of the first and second subsets of light sources.

2. The method of claim 1 wherein the general lighting comprises:
   a. interior lighting;
   b. exterior lighting;
   c. general purpose lighting, or
   d. background lighting.

3. The method of claim 1 wherein the lower melanopic content comprises melanopic content effective to produce a sleepiness response in melanopic receptors; and the higher melanopic content comprises melanopic content effective to produce an alertness response in melanopic receptors.

4. The method of claim 1 wherein the selective driving for circadian lighting is according to a predefined profile, wherein
   the predefined profile transitions between higher and lower melanopic content by the selectively driving of the first and second subsets of light sources.

5. The method of claim 4 wherein the transitions are based on at least one of:
   a. predetermined time intervals;
   b. sensed measurements;
   c. remotely controlled instructions.

6. The method of claim 1 wherein the first subset configured to provide higher melanopic content has a relatively high percentage of energy in a band around 488 nm, wherein on a scale normalized to 1 said energy is at or above on the order of 0.20 between 478 to 498 nm.

7. The method of claim 6 wherein said energy is at or above on the order of 0.30 between 483 to 493 nm.

8. The method of claim 7 wherein said energy is at or above on the order of 0.40 between 486 to 490 nm.

9. The method of claim 1 wherein the higher and lower melanopic content comprises a calculated melanopic/photopic (M/P) value related to spectral power distribution (SPD) of the light sources.

10. The method of claim 1 wherein the set of light sources is embodied in a plurality of light fixtures, luminaires, or modules aimed to provide illumination of at least a portion of the area or space at the area.

\* \* \* \* \*